US009181589B2

(12) United States Patent
Libutti et al.

(10) Patent No.: US 9,181,589 B2
(45) Date of Patent: Nov. 10, 2015

(54) MOLECULAR-BASED METHOD OF CANCER DIAGNOSIS AND PROGNOSIS

(71) Applicant: The United States of America, as represented by the Secretary, Department of Health and Human Services, Washington, DC (US)

(72) Inventors: Steven K. Libutti, Bronx, NY (US); Mei He, Rockville, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 14/215,574

(22) Filed: Mar. 17, 2014

(65) Prior Publication Data
US 2014/0200160 A1 Jul. 17, 2014

Related U.S. Application Data

(62) Division of application No. 13/148,851, filed as application No. PCT/US2010/024026 on Feb. 12, 2010, now Pat. No. 8,715,928.

(60) Provisional application No. 61/152,597, filed on Feb. 13, 2009.

(51) Int. Cl.
*C12Q 1/68* (2006.01)
*C12P 21/06* (2006.01)
*A61K 39/395* (2006.01)
*G01N 33/574* (2006.01)

(52) U.S. Cl.
CPC ........ *C12Q 1/6886* (2013.01); *G01N 33/57415* (2013.01); *G01N 33/57419* (2013.01); *G01N 33/57423* (2013.01); *G01N 33/57434* (2013.01); *C12Q 2600/118* (2013.01); *C12Q 2600/158* (2013.01); *G01N 2800/56* (2013.01)

(58) Field of Classification Search
None
See application file for complete search history.

(56) References Cited

U.S. PATENT DOCUMENTS

| | | | |
|---|---|---|---|
| 6,586,581 B1 | 7/2003 | Bancroft et al. | |
| 6,706,867 B1 | 3/2004 | Lorenz | |
| 7,171,311 B2 | 1/2007 | Dai et al. | |
| 2005/0227917 A1 | 10/2005 | Williams et al. | |
| 2006/0183141 A1 | 8/2006 | Chang et al. | |
| 2007/0117164 A1 | 5/2007 | Raskov et al. | |
| 2007/0178458 A1 | 8/2007 | O'Brien et al. | |
| 2009/0215709 A1 | 8/2009 | Van Criekinge et al. | |

FOREIGN PATENT DOCUMENTS

| | | |
|---|---|---|
| WO | WO 02/31209 | 4/2002 |
| WO | WO 03/040296 | 5/2003 |
| WO | WO 2004/079014 | 9/2004 |
| WO | WO 2004/097052 | 11/2004 |
| WO | WO 2006/060653 | 6/2006 |
| WO | WO 2006/135886 | 12/2006 |
| WO | WO 2007/142936 | 12/2007 |
| WO | WO 2008/077165 | 7/2008 |
| WO | WO 2008/089577 | 7/2008 |
| WO | WO 2008/157383 | 12/2008 |

OTHER PUBLICATIONS

Jamieson Dissertation entitled Cell Surface Characterization of Neural Stem Cells and Brain Tumour Stem Cells (Aug. 2008).*
Wang Dissertation entitled Analysis of the Mixed Lineage Leukemia Protein in Transcriptional Regulation and Leukemogenesis (2005).*
Applied Microarrays "CodeLink Human Whole Genome Bioarray," http://www.appliedmicroarrays.com/back_up/300026%20-%20 CodeLink%20Human%20Whole%20Genome%20Bioarray.pdf, 2007.
Chang et al., "Gene Expression Signature of Fibroblast Serum Response Predicts Human Cancer Progression: Similarities between Tumors and Wounds," *PLoS Biol.*, vol. 2, pp. 0206-0214, 2004.
Chang et al., "Robustness, Scalability, and Integration of a Wound-Response Gene Expression Signature in Predicting Breast Cancer Survival," *Proc. Natl. Acad. Sci. USA*, vol. 102, pp. 3738-3743, 2005.
Gillett "Microarray Expression Profiling of ABC Transporters in Human Breast Cancer," *Cancer Genomics & Proteomics*, vol. 3, pp. 97-106, 2006.
Hemstreet et al., "Selection and Development of Biomarkers for Bladder Cancer," In *Methods in Molecular Medicine: Tumor Marker Protocols*, Eds., Hanausek and Walaszek, pp. 37-60, 1998.
Ishkanian et al., "A tiling resolution DNA microarray with complete coverage of the human genome," *Nature Genetics*, vol. 36, No. 3, pp. 299-303, 2004.
Ivshina et al., "Genetic Reclassification of Histologic Grade Delineates New Clinical Subtypes of Breast Cancer," *Cancer Res.*, vol. 66, pp. 10292-10301, 2006.
Liu et al., "The Prognostic Role of a Gene Signature from Tumorigenic Breast-Cancer Cells," *N. Engl. J. Med.*, vol. 356, pp. 217-226, 2007.
Pawitan et al., "Gene Expression Profiling Spares Early Breast Cancer Patients from Adjuvant Therapy: Derived and Validated in Two Population-Based Cohorts," *Breast Cancer Research*, vol. 7, pp. R953-R964, 2005.

(Continued)

*Primary Examiner* — Catherine S Hibbert
(74) *Attorney, Agent, or Firm* — Klarquist Sparkman, LLP

(57) ABSTRACT

A gene profiling signature for diagnosis and prognosis of cancer patients is disclosed herein. In one embodiment, the gene signature includes 32 or 79 cancer survival factor-associated genes. Thus, provided herein is a method of determining the prognosis of a subject with a tumor by detecting expression of five of more cancer survival factor-associated genes in a tumor sample and comparing expression of the five or more cancer survival factor-associated genes in the tumor sample to a control. In some examples, an increase in expression of ABCF1, CORO1C, DPP3, PREB, UBE3A, and PTDSS1 in a tumor sample compared to a control sample indicates poor prognosis. Further provided are arrays including probes or antibodies specific for a plurality of cancer survival factor-associated genes or proteins.

14 Claims, 8 Drawing Sheets

(56) References Cited

OTHER PUBLICATIONS

Raponi et al., "Gene Expression Signatures for Predicting Prognosis of Squamous Cell and Adenocarcinomas of the Lung," *Cancer Res.*, vol. 66, pp. 7466-7472, 2006.

Sotiriou et al., "Gene Expression Profiling in Breast Cancer: Understanding the Molecular Basis of Histologic Grade to Improve Prognosis," *J. Natl. Cancer Inst.*, vol. 98, pp. 262-272, 2006.

van de Vijver et al., "A Gene Expression Signature as a Predictor of Survival in Breast Cancer," *N. Engl. J. Med.*, vol. 347, pp. 1999-2009, 2002.

van't Veer et al., "Gene Expression Profiling Predicts Clinical Outcome of Breast Cancer," *Nature*, vol. 415, pp. 530-536, 2002.

Winter et al., "Relation of a Hypoxia Metagene Derived from Head and Neck Cancer to Prognosis of Multiple Cancers," *Cancer Research*, vol. 67, No. 7, pp. 3441-3449, 2007.

* cited by examiner

FIG. 3A
van de Vijver
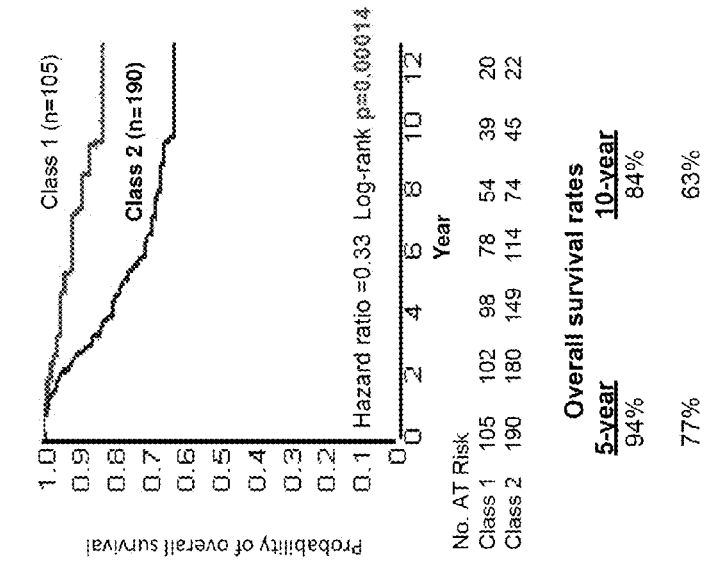
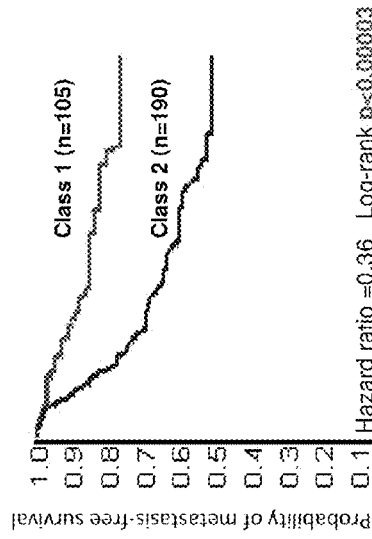

GSE4922

GSE2034

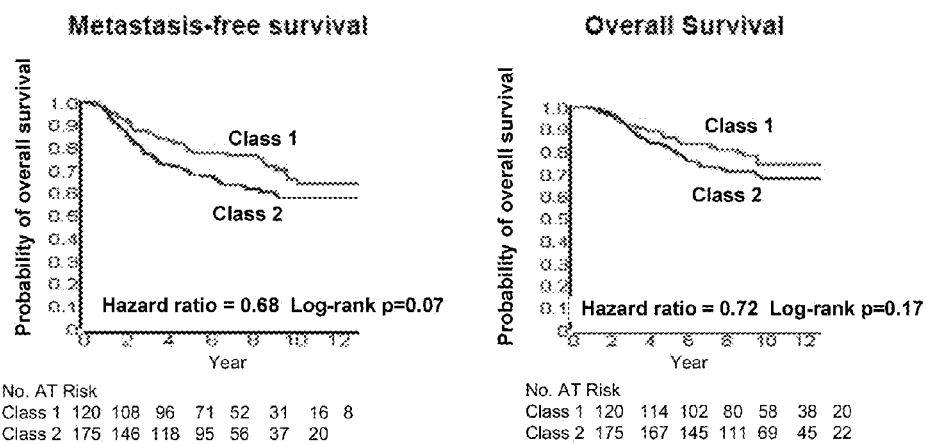
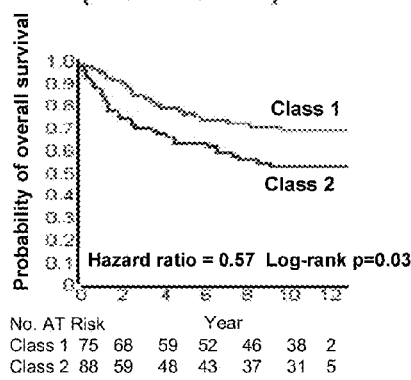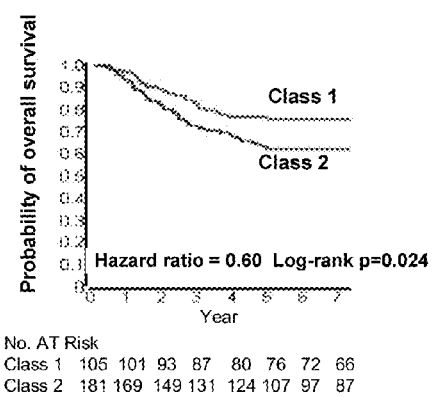

FIG. 5A
Original Datasets
van de Vijver
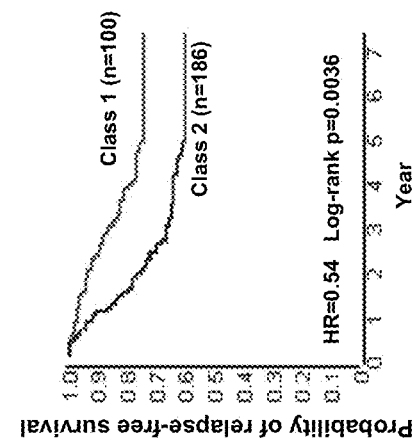
GSE4922
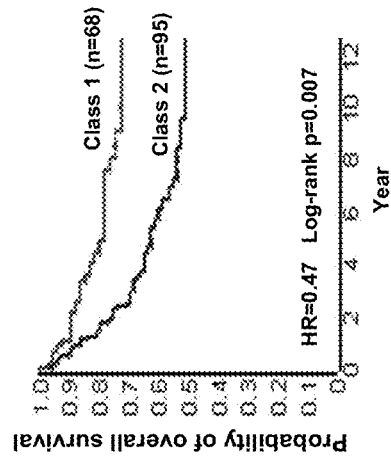
GSE2034
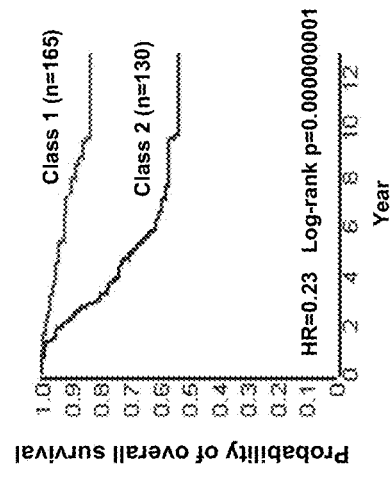

FIG. 5B
Independent validation-sets
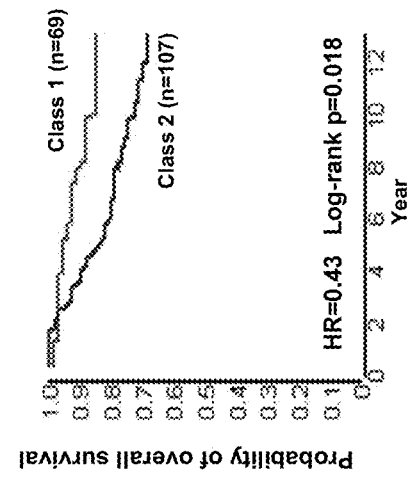
GSE7390
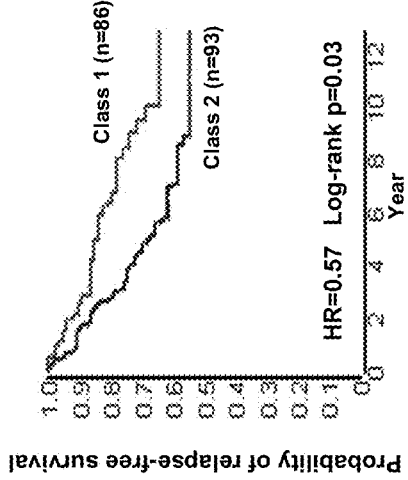
GSE2990
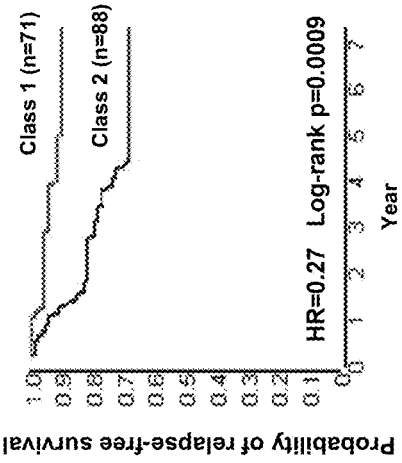
GSE1456

FIG. 6
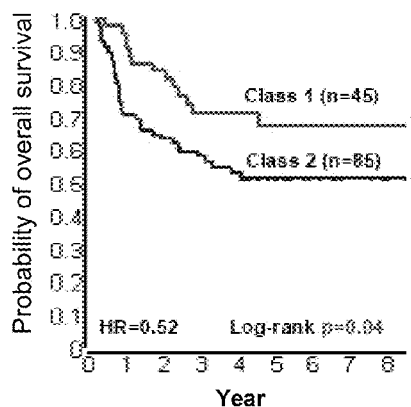
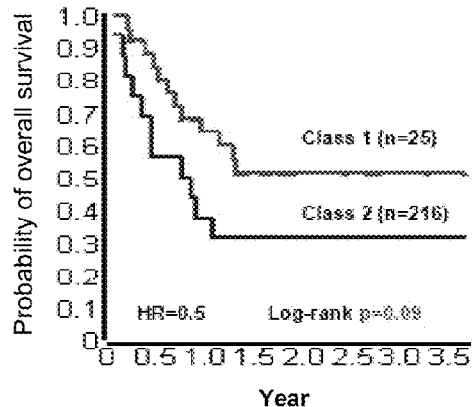
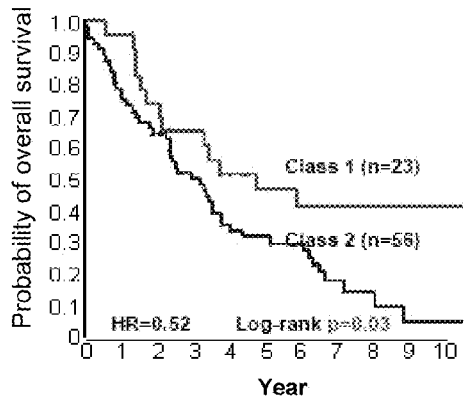
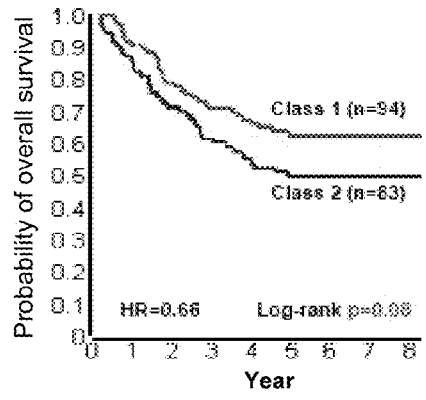
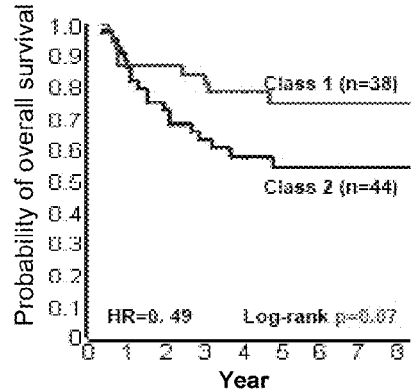
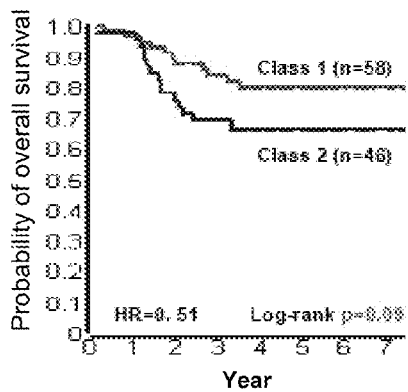

MOLECULAR-BASED METHOD OF CANCER DIAGNOSIS AND PROGNOSIS

CROSS REFERENCE TO RELATED APPLICATIONS

This is a divisional of application Ser. No. 13/148,851, filed Aug. 10, 2011, which is the §371 U.S. National Stage of International Application No. PCT/US2010/024026, filed Feb. 12, 2010, which was published in English under PCT Article 21(2), which in turn claims the benefit of U.S. Provisional Application No. 61/152,597, filed Feb. 13, 2009, which is incorporated by reference herein in its entirety.

FIELD

This disclosure relates to the field of cancer and particularly to methods for diagnosing and determining the prognosis of patients with a tumor.

BACKGROUND

Cancer is responsible for about one third of all mortalities in the United States, while metastatic disease is responsible for more than 90% of all cancer-related deaths (Sporn, *Lancet* 347:1377-1381, 1996). Cellular abnormalities have been organized into six basic competency traits that must be acquired for a malignancy to thrive: self-sufficiency in growth signals, insensitivity to anti-proliferative signals, evasion of apoptosis, limitless replicative potential, sustained angiogenesis, and tissue invasion and metastasis (Hanahan and Weinberg, *Cell* 100:57-70, 2000). These competencies are thought to be the product of alterations attained by the tumor early in the clinical timeline. Coupled with the increasing heterogeneity of the tumor cell population over time, multiple phenotypes may arise with varying levels and tendencies of metastatic competency (Fidler, *Nature Rev. Cancer* 3:453-458, 2003).

Animal models have added to the current understanding of malignant and metastatic progression. The use of different models and techniques, such as in vivo passaging for phenotype purification, transgenic animals for specific molecular manipulation, and in vivo and ex vivo models for screening of cancer therapies has led to functional insights that have allowed development of useful models regarding the causes of malignancy and how to further investigate malignant behavior.

Another valuable and recent breakthrough over the past ten years has been the development and use of high throughput assays, such as microarray expression analysis. Molecular profiling with this technology has gained acclaim and some utility in the management of select cancer patients. Several gene expression-based assays are now marketed for improved prognostic accuracy for patients with breast cancer (Driouch et al., *Clin. Exp. Metastasis* 24:575-585, 2007).

SUMMARY

Disclosed herein is a gene expression signature that can be used for determining the prognosis of a subject with a tumor, such as a breast tumor or lung tumor. In some examples, determining the prognosis includes determining whether a tumor is benign or malignant. In other examples, determining the prognosis includes predicting the outcome of a subject with a tumor. In one example, the gene expression signature includes 32 or 79 genes whose expression is associated with poor survival in subjects with breast cancer. In another example, the gene expression signature includes six genes whose expression is associated with poor survival in subjects with breast cancer or lung cancer. The disclosed gene expression signatures are highly predictive of survival outcomes, and are applicable to multiple tumor types. In particular, the six-gene signature is especially predictive of survival and could be utilized as a rapid and inexpensive hospital-based assay, in contrast to currently available expensive extramural assays. The ability of the gene signatures to reliably predict survival (including metastasis-free survival) provides a particularly useful tool for selecting patient for suitable treatment consistent with the likely progression of their disease.

Methods are disclosed for predicting a clinical outcome in a subject with a tumor (for example, a breast tumor or lung tumor). In an example, the methods include detecting expression of at least five cancer survival factor-associated molecules listed in Table 1, Table 2, Table 6, or combinations thereof (such as at least 5, at least 6, or at least 12 of such molecules) in a tumor sample obtained from the subject with the tumor. The methods also include comparing expression of the at least five cancer survival factor-associated molecules in the tumor sample to a control, wherein an alteration in the expression (such as an at least about 1.5-fold increase in expression) of the at least five cancer survival factor-associated molecules indicates that the subject has a poor prognosis. For example, an alteration in the expression, such as an increase in the expression (for example, an increase of at least about 1.5-fold), of ATP-binding cassette, subfamily F, member 1 (ABCF1); coronin, actin binding protein, 1C (CORO1C); dipeptidyl-peptidase 3 (DPP3); prolactin regulatory binding-element protein (PREB); ubiquitin protein ligase E3A (UBE3A); phosphatidylserine synthase 1 (PTDSS1); or a combination thereof (such as five or more, or all) indicates a poor prognosis, such as a decreased chance of survival. In one example, a decreased chance of survival includes decreased overall survival, decreased metastasis-free survival, or decreased relapse-free survival. Alterations in expression can be measured using methods known in the art, and this disclosure is not limited to particular methods. For example, expression can be measured at the nucleic acid level (such as by real time quantitative polymerase chain reaction or microarray analysis) or at the protein level (such as by Western blot or other immunoassay analysis).

Also disclosed herein are methods for determining whether a subject has a malignant or benign tumor (for example, a breast tumor or lung tumor). In an example, the methods include detecting expression of at least five cancer survival factor-associated molecules listed in Table 1, Table 2, Table 6, or combinations thereof (such as at least 5, at least 6, or at least 12 of such molecules) in a tumor sample obtained from the subject with the tumor. The methods also include comparing expression of the at least five cancer survival factor-associated molecules in the tumor sample to a control, wherein an alteration in the expression (such as an increase of at least about 1.5-fold) of the at least five cancer survival factor-associated molecules indicates that the subject has a malignant tumor. For example, an alteration in the expression, such as an increase in the expression of five or more of ABCF1, CORO1C, DPP3, PREB, UBE3A, PTDSS1, or a combination thereof indicates the tumor is malignant, such as a malignant breast tumor or a malignant lung tumor.

The foregoing and other features of the disclosure will become more apparent from the following detailed description of several embodiments, which proceeds with reference to the accompanying figures.

BRIEF DESCRIPTION OF THE DRAWINGS

FIG. 3A shows two Kaplan-Meier plots of metastasis-free survival (left) and overall survival (right) of patients expressing SpMGS in the van de Vijver dataset. Patients who exhibited the SpMGS signature were assigned class 2, whereas those who did not were assigned class 1.

FIG. 4A shows two Kaplan-Meier plots of metastasis-free survival (left) and overall survival (right) of patients expressing EMGS in the van de Vijver dataset. Patients exhibiting the EMGS signature were assigned Class 2, while those that did not were assigned Class 1.

FIG. 4B is a Kaplan-Meier plot of overall survival of patients expressing EMGS in the GSE4922 dataset. Patients exhibiting the EMGS signature were assigned Class 2, while those that did not were assigned Class 1.

FIG. 4C is a Kaplan-Meier plot of relapse-free survival of patients expressing EMGS in the GSE2034 dataset. Patients exhibiting the EMGS signature were assigned Class 2, while those that did not were assigned Class 1.

FIG. 5A is a series of Kaplan-Meier plots showing survival analysis in the original datasets, based on the SpMGS 6-gene model. Class 2 included patients who exhibited the 6-gene signature and class 1 included patients who did not.

FIG. 5B is a series of Kaplan-Meier plots showing survival analysis in three independent datasets, based on the SpMGS 6-gene model. Class 2 included patients who exhibited the 6-gene signature and class 1 included patients who did not.

FIG. 6 is a series of Kaplan-Meier plots showing survival analysis in six lung cancer datasets, based on the SpMGS 6-gene model. Class 2 included patients who exhibited the 6-gene signature and class 1 included patients who did not. HLM, Moffitt Cancer Center dataset; MICH, University of Michigan Cancer Center dataset; DFCI, Dana Farber Cancer Institute dataset; MSKCC, Memorial Sloan-Kettering Cancer Center dataset.

DETAILED DESCRIPTION

Figure 1:
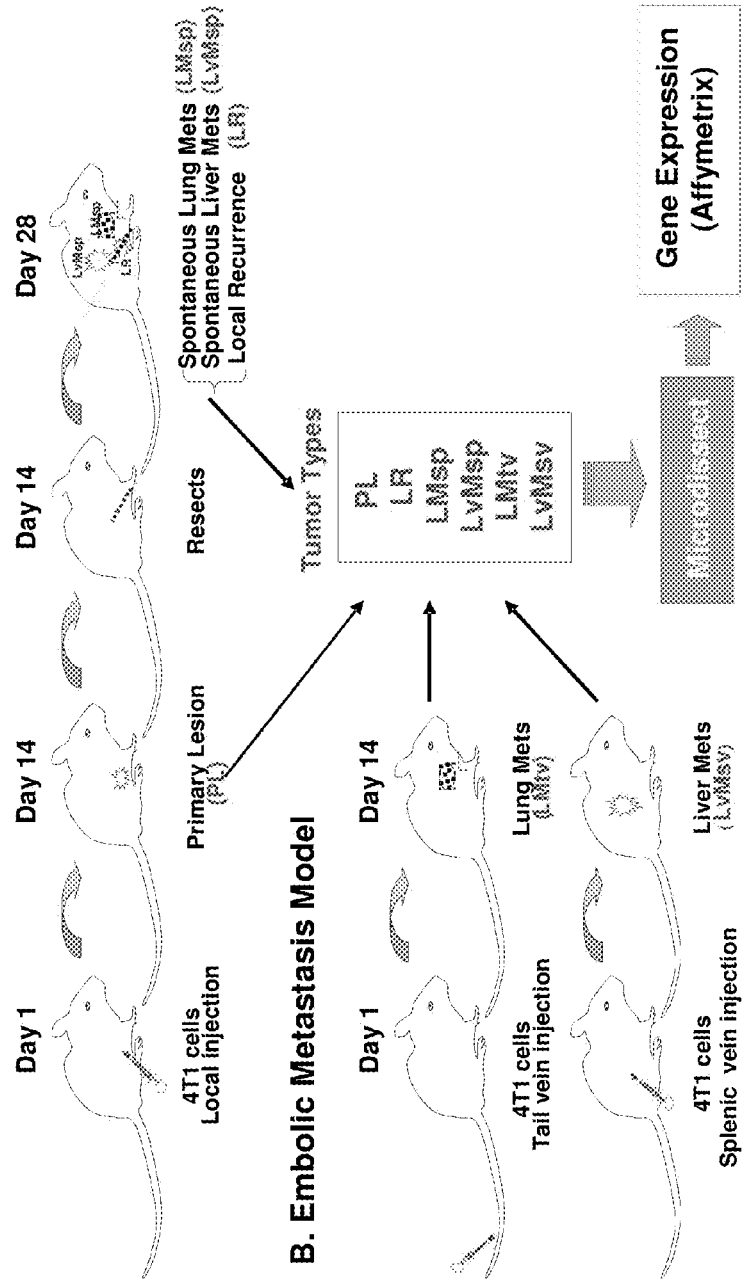
FIG. 1 is a diagram showing the generation of mouse spontaneous and embolic metastasis models.

There is a need for prognostic and diagnostic classifiers that can reliably stratify tumor subjects for therapy, as well as new targets for therapeutic intervention of cancer. Metastatic disease is responsible for more than 90% of all cancer-related deaths, therefore identification of genes that predict likelihood of metastasis is useful for determining the prognosis and selecting therapy for a patient with a tumor, as well as providing new therapeutic targets.

In devising a model that accurately identifies the genetic perturbations responsible for metastases, differential expression between the primary and metastatic lesions is not enough. For example, breast cancer growing in lung tissue should have tissue-specific alterations in gene expression regardless of how it arrived there. This ambient organ-imposed expression alteration confounds a straightforward approach towards detecting metastatic competency genes (MCG). It is shown herein that by subtracting the ambient gene profile from the primary tumor and spontaneously metastatic tumor gene profiles, a MCG profile found in the spontaneously metastasizing cancer can be identified. Embolic lung and liver mouse models served to provide the respective ambient gene profiles (embolic metastasis gene signature; EMGS). Incorporating multiple tropisms (lung and liver) allowed internally generated controls for genetic interpretive quality assessment. In addition, it allowed categorization of gene sets into tropism-specific MCG if they were unique to specific organ tropisms, or general MCG if they were present in both tropisms. The spontaneous metastasis gene signature (SpMGS) represents the theoretical general MCG.

Gene profiling assays have proven extremely important to the clinical management of early breast cancer patients. The two commercially available assays have allowed identification of patients who are at low risk for recurrence, and subsequently may forego adjuvant chemotherapy with its associated morbidity (van't Veer et al., *Nature* 415:530-536, 2002; van de Vijver et al., *N. Engl. J. Med.* 347:1999-2009, 2002). The gene signature provided herein offers a similar utility, with a potentially smaller number of genes than current assays. It is amenable to transformation into a rapid and inexpensive hospital-based assay.

I. Terms and Abbreviations

ABCF1: ATP-binding cassette, sub-family F, member 1
CORO1C: coronin, actin binding protein, 1C
DPP3: dipeptidyl-peptidase 3
EMGS: embolic metastasis gene signature
HR: hazard ratio
ISH: in situ hybridization
LMsp: spontaneous lung metastases
LMtv: lung metastases tail vein model
LR: local recurrence
LvMsp: spontaneous liver metastases
LvMsv: liver metastases splenic vein model
MCG: metastatic competency gene
PREB: prolactin regulatory binding-element protein
PTDSS1: phosphatidylserine synthase 1
SpMGS: spontaneous metastasis gene signature
UBE3A: ubiquitin protein ligase E3A The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. For example, the term "comprising a nucleic acid molecule" includes single or plural nucleic acid molecules and is considered equivalent to the phrase "comprising at least one nucleic acid molecule." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements.

Unless explained otherwise, all technical and scientific terms used herein have the same meaning as commonly understood to one of ordinary skill in the art to which this disclosure belongs. All GenBank Accession Nos. mentioned herein are incorporated by reference in their entirety. Although methods and materials similar or equivalent to those described herein can be used in the practice or testing of the present disclosure, suitable methods and materials are described below. The materials, methods, and examples are illustrative only and not intended to be limiting.

Antibody: A polypeptide including at least a light chain or heavy chain immunoglobulin variable region which specifically recognizes and binds an epitope of an antigen, such as a cancer survival factor-associated molecule or a fragment thereof. Antibodies are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody. Antibodies of the present disclosure include those that are specific for the molecules listed in Tables 1, 2, or 6.

The term antibody includes intact immunoglobulins, as well the variants and portions thereof, such as Fab' fragments, F(ab)'$_2$ fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies (for example, humanized murine antibodies), heteroconjugate antibodies (such as, bispecific antibodies). See also, *Pierce Catalog and Handbook,* 1994-1995 (Pierce Chemical Co., Rockford, Ill.); Kuby, J., *Immunology,* 3$^{rd}$ Ed., W.H. Freeman & Co., New York, 1997.

Typically, a naturally occurring immunoglobulin has heavy (H) chains and light (L) chains interconnected by disulfide bonds. There are two types of light chain, lambda ($\lambda$) and kappa ($\kappa$). There are five main heavy chain classes (or isotypes) which determine the functional activity of an antibody molecule: IgM, IgD, IgG, IgA and IgE.

Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs."

References to "$V_H$" or "VH" refer to the variable region of an immunoglobulin heavy chain, including that of an Fv, scFv, dsFv or Fab. References to "$V_L$" or "VL" refer to the variable region of an immunoglobulin light chain, including that of an Fv, scFv, dsFv or Fab.

A "monoclonal antibody" is an antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

A "polyclonal antibody" is an antibody that is derived from different B-cell lines. Polyclonal antibodies are a mixture of immunoglobulin molecules secreted against a specific antigen, each recognizing a different epitope. These antibodies are produced by methods known to those of skill in the art, for instance, by injection of an antigen into a suitable mammal (such as a mouse, rabbit or goat) that induces the B-lymphocytes to produce IgG immunoglobulins specific for the antigen, which are then purified from the mammal's serum.

A "chimeric antibody" has framework residues from one species, such as human, and CDRs (which generally confer antigen binding) from another species, such as a murine antibody that specifically binds a cancer survival factor-associated molecule.

A "humanized" immunoglobulin is an immunoglobulin including a human framework region and one or more CDRs from a non-human (for example a mouse, rat, or synthetic) immunoglobulin. The non-human immunoglobulin providing the CDRs is termed a "donor," and the human immunoglobulin providing the framework is termed an "acceptor." In one example, all the CDRs are from the donor immunoglobulin in a humanized immunoglobulin. Constant regions need not be present, but if they are, they are substantially identical to human immunoglobulin constant regions, e.g., at least about 85-90%, such as about 95% or more identical. Hence, all parts of a humanized immunoglobulin, except possibly the CDRs, are substantially identical to corresponding parts of natural human immunoglobulin sequences. Humanized immunoglobulins can be constructed by means of genetic engineering (see for example, U.S. Pat. No. 5,585,089).

Array: An arrangement of molecules, such as biological macromolecules (such as peptides or nucleic acid molecules) or biological samples (such as tissue sections), in addressable locations on or in a substrate. A "microarray" is an array that is miniaturized so as to require or be aided by microscopic examination for evaluation or analysis. Arrays are sometimes called chips or biochips.

The array of molecules ("features") makes it possible to carry out a very large number of analyses on a sample at one time. In certain example arrays, one or more molecules (such as an oligonucleotide probe) will occur on the array a plurality of times (such as twice), for instance to provide internal controls. The number of addressable locations on the array can vary, for example from at least one, to at least 2, to at least 5, to at least 10, at least 20, at least 30, at least 50, at least 75, at least 100, at least 150, at least 200, at least 300, at least 500, least 550, at least 600, at least 800, at least 1000, at least 10,000, or more. In particular examples, an array includes nucleic acid molecules, such as oligonucleotide sequences that are at least 15 nucleotides in length, such as about 15-40 nucleotides in length. In particular examples, an array includes oligonucleotide probes or primers which can be used to detect cancer survival factor-associated molecule sequences, such as at least one of those of the sequences listed in Table 1, Table 2, or Table 6, such as at least 2, at least 3, at least 4, at least 5, at least 6, at least 7, at least 10, at least 12, at least 20, at least 30, at least 40, at least 50, at least 60, at least 70, or at least 79 sequences listed in Table 1, Table 2, or Table 6 (for example, 2, 3, 4, 5, 6, 7, 8, 9, 10, 11, 12, 13, 14, 15, 16, 17, 18, 19, 20, 25, 30, 32, 35, 40, 45, 50, 55, 60, 65, 70, 75, or 79 of those listed).

Within an array, each arrayed sample is addressable, in that its location can be reliably and consistently determined within at least two dimensions of the array. The feature application location on an array can assume different shapes. For example, the array can be regular (such as arranged in uniform rows and columns) or irregular. Thus, in ordered arrays the location of each sample is assigned to the sample at the time when it is applied to the array, and a key may be provided in order to correlate each location with the appropriate target or feature position. Often, ordered arrays are arranged in a symmetrical grid pattern, but samples could be arranged in other patterns (such as in radially distributed lines, spiral lines, or ordered clusters). Addressable arrays usually are computer readable, in that a computer can be programmed to correlate a particular address on the array with information about the sample at that position (such as hybridization or binding data, including for instance signal intensity). In some examples of computer readable formats, the individual features in the array are arranged regularly, for instance in a Cartesian grid pattern, which can be correlated to address information by a computer.

Protein-based arrays include probe molecules that are or include proteins, or where the target molecules are or include proteins, and arrays including nucleic acids to which proteins are bound, or vice versa. In some examples, an array contains antibodies to cancer survival factor-associated proteins, such as any combination of those sequences listed in Table 1, Table 2, or Table 6, such as at least 2, at least 3, at least 4, at least 5, at least 6, at least 7, at least 10, at least 12, at least 20, at least 30, at least 40, at least 50, at least 60, at least 70, or at least 79 sequences listed in Table 1, Table 2, or Table 6 (for example, 2, 3, 4, 5, 6, 7, 8, 9, 10, 11, 12, 13, 14, 15, 16, 17, 18, 19, 20, 25, 30, 32, 35, 40, 45, 50, 55, 60, 65, 70, 75, or 79 of those listed).

In some examples, the array includes positive controls, negative controls, or both, for example molecules specific for detecting β-actin, 18S RNA, beta-microglobulin, glyceraldehyde-3-phosphate-dehydrogenase (GAPDH), and other housekeeping genes. In one example, the array includes 1 to 20 controls, such as 1 to 10 or 1 to 5 controls.

ATP-binding cassette, sub-family F, member 1 (ABCF1): A member of the superfamily of ATP-binding cassette (ABC) transporters, also known as ABC27 or ABC50. ABCF1 is a member of the GCN20 sub-family of ABC transporters and lacks membrane spanning domains. The protein interacts with eukaryotic initiation factor 2 and may play a role in protein synthesis. ABCF1 may also be regulated by tumor necrosis factor α, and thus may also be involved in inflammation.

Nucleic acid and protein sequences for ABCF1 are publicly available. For example, GENBANK® Accession Nos.: NM_001025091, NM_001090, BC112923, and BC034488 disclose ABCF1 nucleic acid sequences, and GENBANK® Accession Nos.: NP_001020262, NP_001081, AAI12924, and AAH34488 disclose ABCF1 protein sequences, all of which are incorporated by reference as provided by GENBANK® on Feb. 13, 2009.

In one example, ABCF1 includes a full-length wild-type (or native) sequence, as well as ABCF1 allelic variants that retain the ability to be expressed at increased levels in a tumor and/or modulate an activity of a tumor, such as metastatic potential. In certain examples, ABCF1 has at least 80% sequence identity, for example at least 85%, 90%, 95%, or 98% sequence identity to a publicly available ABCF1 sequence.

Breast cancer: A neoplastic condition of breast tissue that can be benign or malignant. The most common type of breast cancer is ductal carcinoma. Ductal carcinoma in situ is a non-invasive neoplastic condition of the ducts. Lobular carcinoma is not an invasive disease but is an indicator that a carcinoma may develop. Infiltrating (malignant) carcinoma of the breast can be divided into stages (I, IIA, IIB, IIIA, IIIB, and IV).

Surgery is a treatment for a breast tumor and is frequently necessary for diagnosis. The type of surgery depends upon how widespread the tumor is when diagnosed (the tumor stage), as well as the type and grade of tumor. The surgeon may perform a lumpectomy, mastectomy, bilateral mastectomy. Chemotherapy is often used after surgery to treat any residual disease. Systemic chemotherapy often includes a platinum derivative with a taxane. Chemotherapy is also used to treat subjects who have a recurrence or metastasis.

Cancer: A malignant neoplasm that has undergone characteristic anaplasia with loss of differentiation, increased rate of growth, invasion of surrounding tissue, and is capable of metastasis. For example, breast cancer is a malignant neoplasm that arises in or from breast tissue (such as a ductal carcinoma) and lung cancer is a malignant neoplasm that arises in or from lung tissue (such as non-small cell lung cancer or small cell lung cancer). In other examples, prostate cancer is a malignant neoplasm that arises in or from prostate tissue and colorectal cancer is cancer that arises in or from large bowel (colon or rectal tissue).

Residual cancer is cancer that remains in a subject after any form of treatment given to the subject to reduce or eradicate cancer. Metastatic cancer is a cancer at one or more sites in the body other than the site of origin of the original (primary) cancer from which the metastatic cancer is derived. Local recurrence is reoccurrence of the cancer at or near the same site (such as in the same tissue) as the original cancer.

Cancer survival factor-associated (or related) molecule: A molecule whose expression is altered in a tumor cell (such as a metastatic tumor cell). Such molecules include, for instance, nucleic acid sequences (such as DNA, cDNA, or mRNAs) and proteins. Specific genes include those listed in Tables 1 and 2, as well as fragments of the full-length genes, cDNAs, or mRNAs (and proteins encoded thereby) whose expression is altered (such as upregulated or downregulated) in response to a tumor, including a breast tumor or lung tumor. Thus, the presence or absence of the respective cancer survival factor-associated molecules can be used to diagnose and/or determine the prognosis of a tumor in a subject as well as to treat a subject with a tumor, such as a breast tumor or lung tumor.

In an example, a cancer survival factor-associated molecule is any molecule listed in Tables 1 and 2. Specific examples of cancer (such as breast cancer or lung cancer) survival factor-associated molecules that are upregulated in a subject with a poor prognosis include ATP-binding cassette, subfamily F, member 1 (ABCF1); coronin, actin binding protein, 1C (CORO1C); dipeptidyl-peptidase 3 (DPP3); prolactin regulatory binding-element protein (PREB); ubiquitin protein ligase E3A (UBE3A); or phosphatidylserine synthase 1 (PTDSS1).

Cancer survival factor-associated molecules can be involved in or influenced by cancer in different ways, including causative (in that a change in a cancer survival factor-associated molecule leads to development of or progression of cancer) or resultive (in that development of or progression of cancer causes or results in a change in the cancer survival factor-associated molecule).

Consists essentially of: In the context of the present disclosure, "consists essentially of" indicates that the expression of additional cancer survival factor-associated genes can be evaluated, but not more than ten additional cancer survival factor-associated genes. In some examples, "consists essentially of" indicates that no more than 5 other molecules are evaluated, such as no more than 4, 3, 2, or 1 other molecules. In some examples, fewer than the recited molecules are evaluated, but not less than 4, 3, 2 or 1 fewer molecules. In some examples, the expression of one or more controls is evaluated, such as a housekeeping protein or rRNA (such as 18S RNA, beta-microglobulin, GAPDH, and/or β-actin). In this context "consists of" indicates that only the expression of the stated molecules is evaluated; the expression of additional molecules is not evaluated.

Control: A "control" refers to a sample or standard used for comparison with an experimental sample. In some embodiments, the control is a sample obtained from a healthy patient or a non-tumor tissue sample obtained from a patient diagnosed with cancer. In some embodiments, the control is a historical control or standard reference value or range of values (such as a previously tested control sample, such as a group of cancer patients with poor prognosis, or group of samples that represent baseline or normal values, such as the level of cancer-associated genes in non-tumor tissue).

Coronin, actin binding protein, 1C (CORO1C): The protein encoded by this gene is a member of the coronin-like family and contains five WD repeats. CORO1C is also known as coronin 3. CORO1C is ubiquitously expressed, associates with F-actin and is likely to be involved in cytokinesis, motility, and signal transduction, as are other members of this family.

Nucleic acid and protein sequences for CORO1C are publicly available. For example, GENBANK® Accession Nos.: NM_014325, BC002342, and AB030656 disclose CORO1C nucleic acid sequences, and GENBANK® Accession Nos.: NP_055140, AAH02342, and BAA83077 disclose CORO1C protein sequences, all of which are incorporated by reference as provided by GENBANK® on Feb. 13, 2009.

In one example, CORO1C includes a full-length wild-type (or native) sequence, as well as CORO1C allelic variants that retain the ability to be expressed at increased levels in a tumor and/or modulate an activity of a tumor, such as metastatic potential. In certain examples, CORO1C has at least 80% sequence identity, for example at least 85%, 90%, 95%, or 98% sequence identity to a publicly available CORO1C sequence.

Cox hazard ratio: The ratio of survival hazards for a one-unit change in logarithmic gene expression levels. This ratio is derived from the Cox proportional hazards model, which measures the instantaneous force of mortality at any time conditional on having survived until that time. The magnitude of the ratio indicates the degree of impact a one-unit change in the logarithmic gene expression has on patient survival. Thus, a larger value has a greater effect on overall survival. In some examples, a hazard ratio (HR) greater than 1 indicates that increased expression is associated with a reduction in patient survival. In other examples, a HR less than 1 indicates that decreased expression is associated with a reduction in patient survival.

Decrease: To reduce the quality, amount, or strength of something. In one example, a therapy decreases a tumor (such as the size of a tumor, the number of tumors, the metastasis of a tumor, or combinations thereof), or one or more symptoms associated with a tumor, for example as compared to the response in the absence of the therapy (such as a therapy administered to affect tumor size via administration of a binding agent capable of binding to one or more of the cancer survival factor-associated molecules listed in Tables 1, 2, and 6). In a particular example, a therapy decreases the size of a tumor, the number of tumors, the metastasis of a tumor, or combinations thereof, subsequent to the therapy, such as a decrease of at least 10%, at least 20%, at least 50%, or even at least 90%. Such decreases can be measured using the methods disclosed herein. In additional examples, the presence of at least one of the disclosed cancer survival factor-associated molecules decreases a subject's chance of survival.

Detecting expression of a gene product: Determining of a level expression in either a qualitative or quantitative manner can detect nucleic acid molecules or proteins. Exemplary methods include microarray analysis, RT-PCR, Northern blot, Western blot, and mass spectrometry.

Diagnosis: The process of identifying a disease by its signs, symptoms and results of various tests. The conclusion reached through that process is also called "a diagnosis." Forms of testing commonly performed include blood tests, medical imaging, urinalysis, and biopsy. In some examples, a diagnosis includes determining whether a tumor is benign or malignant. In other examples, a diagnosis includes determining whether a subject with cancer has a good or poor prognosis.

Differential or alteration in expression: A difference or change, such as an increase or decrease, in the conversion of the information encoded in a gene (such as a cancer survival factor-associated molecule listed in Tables 1, 2, or 6) into messenger RNA, the conversion of mRNA to a protein, or both. In some examples, the difference is relative to a control or reference value or range of values, such as an amount of gene expression that is expected in a subject who does not have cancer (for example breast cancer or lung cancer) or in non-tumor tissue from a subject with cancer. Detecting differential expression can include measuring a change in gene expression or a change in protein levels.

Dipeptidyl-peptidase 3 (DPP3): A member of the S9B family in clan SC of the serine proteases. DPP3 contains a unique zinc-binding motif and has post-proline dipeptidyl aminopeptidase activity. Increased DPP3 activity has been associated with endometrial and ovarian cancers.

Nucleic acid and protein sequences for DPP3 are publicly available. For example, GENBANK® Accession Nos.: NM_130443, NM_005700, BC001446, BC024271, and AK315478 disclose DPP3 nucleic acid sequences, and GENBANK® Accession Nos.: NP_569710, NP_005691, AAH01446, AAH24271, and BAG37862 disclose DPP3 protein sequences, all of which are incorporated by reference as provided by GENBANK® on Feb. 13, 2009.

In one example, DPP3 includes a full-length wild-type (or native) sequence, as well as DPP3 allelic variants that retain the ability to be expressed at increased levels in a tumor and/or modulate an activity of a tumor, such as metastatic potential. In certain examples, DPP3 has at least 80% sequence identity, for example at least 85%, 90%, 95%, or 98% sequence identity to a publicly available DPP3 sequence.

Downregulated or inactivation: When used in reference to the expression of a nucleic acid molecule, such as a gene, refers to any process which results in a decrease in production of a gene product (such as one or more of those listed in Tables 1, 2, and 6). A gene product can be RNA (such as mRNA, rRNA, tRNA, and structural RNA) or protein. Therefore, gene downregulation or inactivation includes processes that decrease transcription of a gene or translation of mRNA.

Examples of processes that decrease transcription include those that facilitate degradation of a transcription initiation complex, those that decrease transcription initiation rate, those that decrease transcription elongation rate, those that decrease processivity of transcription and those that increase transcriptional repression. Gene downregulation can include reduction of expression below an existing level. Examples of processes that decrease translation include those that decrease translational initiation, those that decrease translational elongation and those that decrease mRNA stability.

Gene downregulation includes any detectable decrease in the production of a gene product. In certain examples, production of a gene product decreases by at least 1.5-fold, such as at least 2-fold, at least 3-fold or at least 4-fold, as compared to a control (such as an amount of gene expression in a normal cell). In one example, a control is a relative amount of gene expression or protein expression in a biological sample taken from a subject who does not have a tumor or a non-tumor sample taken from a subject with a tumor.

Expression: The process by which the coded information of a gene is converted into an operational, non-operational, or structural part of a cell, such as the synthesis of a protein. Gene expression can be influenced by external signals. For instance, exposure of a cell to a hormone may stimulate expression of a hormone-induced gene. Different types of cells can respond differently to an identical signal. Expression of a gene also can be regulated anywhere in the pathway from DNA to RNA to protein. Regulation can include controls on transcription, translation, RNA transport and processing, degradation of intermediary molecules such as mRNA, or through activation, inactivation, compartmentalization or degradation of specific protein molecules after they are produced. In an example, gene expression can be monitored to determine the diagnosis and/or prognosis of a subject with a tumor (such as a breast tumor or lung tumor), such as to determine if a tumor is malignant or to predict a subject's survival or likelihood to develop metastasis.

The expression of a nucleic acid molecule in a test sample can be altered relative to a control sample, such as a normal or non-tumor sample. Alterations in gene expression, such as differential expression, include but are not limited to: (1) overexpression; (2) underexpression; or (3) suppression of expression. Alterations in the expression of a nucleic acid molecule can be associated with, and in fact cause, a change in expression of the corresponding protein.

Protein expression can also be altered in some manner to be different from the expression of the protein in a normal (e.g., non-tumor) situation. This includes but is not necessarily limited to: (1) a mutation in the protein such that one or more of the amino acid residues is different; (2) a short deletion or addition of one or a few (such as no more than 10-20) amino acid residues to the sequence of the protein; (3) a longer deletion or addition of amino acid residues (such as at least 20 residues), such that an entire protein domain or sub-domain is removed or added; (4) expression of an increased amount of the protein compared to a control or standard amount; (5) expression of a decreased amount of the protein compared to a control or standard amount; (6) alteration of the subcellular localization or targeting of the protein; (7) alteration of the temporally regulated expression of the protein (such that the protein is expressed when it normally would not be, or alternatively is not expressed when it normally would be); (8) alteration in stability of a protein through increased longevity in the time that the protein remains localized in a cell; and (9) alteration of the localized (such as organ or tissue specific or subcellular localization) expression of the protein (such that the protein is not expressed where it would normally be expressed or is expressed where it would normally not be expressed), each compared to a control or standard.

Controls or standards for comparison to a sample, for the determination of differential expression, include samples believed to be normal (in that they are not altered for the desired characteristic, for example a sample from a subject who does not have cancer, such as breast cancer or lung cancer) as well as laboratory values (e.g., range of values), even though possibly arbitrarily set, keeping in mind that such values can vary from laboratory to laboratory. Laboratory standards and values can be set based on a known or determined population value and can be supplied in the format of a graph or table that permits comparison of measured, experimentally determined values.

Gene expression profile (or signature): Differential or altered gene expression can be detected by changes in the detectable amount of gene expression (such as cDNA or mRNA) or by changes in the detectable amount of proteins expressed by those genes. A distinct or identifiable pattern of gene expression, for instance a pattern of high and low expression of a defined set of genes or gene-indicative nucleic acids such as ESTs. In some examples, as few as five genes provides a profile, but more genes can be used in a profile, for example, at least 6, at least 10, at least 12, at least 20, at least 25, at least 30, at least 50, at least 70, or more of those listed in Tables 1, 2, and 6. A gene expression profile (also referred to as a signature) can be linked to a tissue or cell type (such as a tumor cell), to a particular stage of normal tissue growth or disease progression (such as advanced cancer), metastatic potential, or to any other distinct or identifiable condition that influences gene expression in a predictable way. Gene expression profiles can include relative as well as absolute expression levels of specific genes, and can be viewed in the context of a test sample compared to a baseline or control sample profile (such as a sample from the same tissue type from a subject who does not have a tumor). In one example, a gene expression profile in a subject is read on an array (such as a nucleic acid or protein array). For example, a gene expression profile can be performed using a commercially available array such as Human Genome GeneChip® arrays from Affymetrix® (Santa Clara, Calif.).

Hybridization: To form base pairs between complementary regions of two strands of DNA, RNA, or between DNA and RNA, thereby forming a duplex molecule, for example. Hybridization conditions resulting in particular degrees of stringency will vary depending upon the nature of the hybridization method and the composition and length of the hybridizing nucleic acid sequences. Generally, the temperature of hybridization and the ionic strength (such as the Na concentration) of the hybridization buffer will determine the stringency of hybridization. Calculations regarding hybridization conditions for attaining particular degrees of stringency are discussed in Sambrook et al., (1989) Molecular Cloning, second edition, Cold Spring Harbor Laboratory, Plainview, N.Y. (chapters 9 and 11). The following is an exemplary set of hybridization conditions and is not limiting:

Very High Stringency (Detects Sequences that Share at Least 90% Identity)

Hybridization: 5×SSC at 65° C. for 16 hours

Wash twice: 2×SSC at room temperature (RT) for 15 minutes each

Wash twice: 0.5×SSC at 65° C. for 20 minutes each

High Stringency (Detects Sequences that Share at Least 80% Identity)

Hybridization: 5×-6×SSC at 65° C.-70° C. for 16-20 hours

Wash twice: 2×SSC at RT for 5-20 minutes each

Wash twice: 1×SSC at 55° C.-70° C. for 30 minutes each

Low Stringency (Detects Sequences that Share at Least 60% Identity)

Hybridization: 6×SSC at RT to 55° C. for 16-20 hours

Wash at least twice: 2×-3×SSC at RT to 55° C. for 20-30 minutes each

Isolated: An "isolated" biological component (such as a nucleic acid molecule, protein, or cell) has been substantially separated or purified away from other biological components in the cell of the organism, or the organism itself, in which the component naturally occurs, such as other chromosomal and extra-chromosomal DNA and RNA, proteins and cells. Nucleic acid molecules and proteins that have been "isolated" include nucleic acid molecules and proteins purified by standard purification methods. The term also embraces nucleic acid molecules and proteins prepared by recombinant expression in a host cell as well as chemically synthesized nucleic acid molecules and proteins. In one example, an isolated cell is a breast cancer cell that is substantially separated from other breast cell subtypes, such as non-cancerous breast cells. In another example, an isolated cell is a lung cancer cell that is substantially separated from other lung cell subtypes, such as non-cancerous lung cells.

Label: An agent capable of detection, for example by ELISA, spectrophotometry, flow cytometry, or microscopy. For example, a label can be attached to a nucleic acid molecule or protein (such as those listed in Table 1, 2, and 6), thereby permitting detection of the nucleic acid molecule or protein. Examples of labels include, but are not limited to, radioactive isotopes, enzyme substrates, co-factors, ligands, chemiluminescent agents, fluorophores, haptens, enzymes, and combinations thereof. Methods for labeling and guidance in the choice of labels appropriate for various purposes are discussed for example in Sambrook et al. (Molecular Cloning: A Laboratory Manual, Cold Spring Harbor, N.Y., 1989) and Ausubel et al. (In Current Protocols in Molecular Biology, John Wiley & Sons, New York, 1998). In a particular example, a label is conjugated to a binding agent that specifically binds to one or more of the cancer survival factor-associated molecules disclosed in Tables 1, 2, and 6 to allow for detecting the presence of a tumor in a subject.

Lung cancer: A neoplastic condition of lung tissue that can be benign or malignant. The majority of lung cancers are non-small cell lung cancer (such as adenocarcinoma of the lung, squamous cell carcinoma, and large-cell cancer). Most other lung cancers are small-cell lung carcinomas. In particular examples, lung cancer includes non-small cell lung cancer.

Malignant: Cells that have the properties of anaplasia, invasion, and metastasis.

Mammal: This term includes both human and non-human mammals. Examples of mammals include, but are not limited to: humans, pigs, cows, goats, cats, dogs, rabbits, rats, and mice.

Metastasis: Cancer cells that have left the original tumor site and migrated to other parts of the body, for example via the bloodstream or lymph system.

Metastasis gene signature: One or more genes that are differentially expressed in a metastasis or a particular type of metastasis relative to another type of tissue (such as non-tumor cells, primary tumor cells, or another metastasis). In one example, the metastasis gene signature is a spontaneous metastasis gene signature (SpMGS), which includes genes that are differentially expressed in one or more spontaneous metastases relative to one or more embolic metastases or local tumor recurrences (for example the genes listed in Table 1 or Table 6). In another example, the metastasis gene signature is an embolic metastasis gene signature (EMGS), which includes genes that are differentially expressed in one or more embolic metastases relative to one or more spontaneous metastases or local tumor recurrences (for example, the genes listed in Table 2 or Table 7).

In some examples, a metastasis gene signature is useful for predicting prognosis of a subject with cancer, wherein the presence of a SpMGS or EMGS in a sample from the subject indicates that the subject has a poor prognosis (for example, decreased chance of survival). In other examples, a metastasis gene signature is useful for diagnosing a subject with cancer, wherein the presence of a SpMGS or EMGS in a sample from the subject indicates that the subject has a malignant tumor.

Nucleic acid array: An arrangement of nucleic acids (such as DNA or RNA) in assigned locations on a matrix, such as that found in cDNA arrays, or oligonucleotide arrays.

Nucleic acid molecules representing genes: Any nucleic acid, for example DNA (intron or exon or both), cDNA, or RNA (such as mRNA), of any length suitable for use as a probe or other indicator molecule, and that is informative about the corresponding gene, such as those listed in Tables 1, 2, or 6.

Phosphatidylserine synthase 1 (PTDSS1): An enzyme involved in the biosynthesis of phosphatidylserine. PTDSS1 utilizes phosphatidylcholine as a substrate for a base-exchange reaction to synthesize phosphatidylserine.

Nucleic acid and protein sequences for PTDSS1 are publicly available. For example, GENBANK® Accession Nos.: NM_014754, BC002376, BC004502, BC004192, and D14694 disclose PTDSS1 nucleic acid sequences, and GENBANK® Accession Nos.: NP_055569, AAH02376, AAH04502, AAH04192, and BAA03520 disclose PTDSS1 protein sequences, all of which are incorporated by reference as provided by GENBANK® on Feb. 13, 2009.

In one example, PTDSS1 includes a full-length wild-type (or native) sequence, as well as PTDSS1 allelic variants that retain the ability to be expressed at increased levels in a tumor and/or modulate an activity of a tumor, such as metastatic potential. In certain examples, PTDSS1 has at least 80% sequence identity, for example at least 85%, 90%, 95%, or 98% sequence identity to a publicly available PTDSS1 sequence.

Polymerase chain reaction (PCR): An in vitro amplification technique that increases the number of copies of a nucleic acid molecule (for example, a nucleic acid molecule in a sample or specimen), such as amplification of a nucleic acid molecule listed in Table 1, 2, or 6. The product of a PCR can be characterized by standard techniques known in the art, such as electrophoresis, restriction endonuclease cleavage patterns, oligonucleotide hybridization or ligation, and/or nucleic acid sequencing.

In some examples, PCR utilizes primers, for example, DNA oligonucleotides 10-100 nucleotides in length, such as about 15, 20, 25, 30 or 50 nucleotides or more in length (such as primers that can be annealed to a complementary target DNA strand by nucleic acid hybridization to form a hybrid between the primer and the target DNA strand, such as those listed in Table 1, 2, or 6). Primers can be selected that include at least 15, at least 20, at least 25, at least 30, at least 35, at least 40, at least 45, at least 50 or more consecutive nucleotides of a cancer survival factor-associated nucleotide sequence.

Methods for preparing and using nucleic acid primers are described, for example, in Sambrook et al. (In *Molecular Cloning: A Laboratory Manual*, CSHL, New York, 1989), Ausubel et al. (ed.) (In *Current Protocols in Molecular Biology*, John Wiley & Sons, New York, 1998), and Innis et al. (*PCR Protocols, A Guide to Methods and Applications*, Academic Press, Inc., San Diego, Calif., 1990).

Prognosis: A prediction of the course of a disease, such as cancer (for example, breast cancer or lung cancer). The prediction can include determining the likelihood of a subject to develop aggressive, recurrent disease, to develop one or more metastases, to survive a particular amount of time (e.g., determine the likelihood that a subject will survive 1, 2, 3 or 5 years), to respond to a particular therapy (e.g., chemotherapy), or combinations thereof. The prediction can also include determining whether a subject has a malignant or a benign tumor.

Prolactin regulatory binding-element protein (PREB): A WD motif transcription factor that binds to a Pit-1-binding element of the prolactin promoter. PREB acts as a transcription factor in the pancreas and adrenal gland as well as the pituitary. PREB may be involved in some of the developmental abnormalities associated with partial trisomy 2p.

Nucleic acid and protein sequences for PREB are publicly available. For example, GENBANK® Accession Nos.: NM_013388, BC016906, BC002765, and AF203687 disclose PREB nucleic acid sequences, and GENBANK® Accession Nos.: NP_037520, AAH16906, AAH02765, and AAF19192 disclose PREB protein sequences, all of which are incorporated by reference as provided by GENBANK® on Feb. 13, 2009.

In one example, PREB includes a full-length wild-type (or native) sequence, as well as PREB allelic variants that retain the ability to be expressed at increased levels in a tumor and/or modulate an activity of a tumor, such as metastatic potential. In certain examples, PREB has at least 80% sequence identity, for example at least 85%, 90%, 95%, or 98% sequence identity to a publicly available PREB sequence.

Sample (or biological sample): A biological specimen containing genomic DNA, RNA (including mRNA), protein, or combinations thereof, obtained from a subject. Examples include, but are not limited to, peripheral blood, fine needle aspirate, urine, saliva, tissue biopsy, surgical specimen, and autopsy material. In one example, a sample includes a tumor biopsy (such as a breast tumor or lung tumor tissue biopsy). In another example, a sample includes isolated tumor cells, such as tumor cells isolated from blood of a subject with a tumor.

Sequence identity/similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215: 403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biotechnology (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site.

BLASTN is used to compare nucleic acid sequences, while BLASTP is used to compare amino acid sequences. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a nucleic acid sequence that has 1166 matches when aligned with a test sequence having 1554 nucleotides is 75.0 percent identical to the test sequence (1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer. In another example, a target sequence containing a 20-nucleotide region that aligns with 20 consecutive nucleotides from an identified sequence as follows contains a region that shares 75 percent sequence identity to that identified sequence (that is, 15÷20*100=75).

For comparisons of amino acid sequences of greater than about 30 amino acids, the Blast 2 sequences function is employed using the default BLOSUM62 matrix set to default parameters, (gap existence cost of 11, and a per residue gap cost of 1). Homologs are typically characterized by possession of at least 70% sequence identity counted over the full-length alignment with an amino acid sequence using the NCBI Basic Blast 2.0, gapped blastp with databases such as the nr or swissprot database. Queries searched with the blastn program are filtered with DUST (Hancock and Armstrong, 1994, *Comput. Appl. Biosci.* 10:67-70). Other programs may use SEG filtering (Wootton and Federhen, *Meth. Enzymol.* 266:554-571, 1996). In addition, a manual alignment can be performed.

Proteins with even greater similarity will show increasing percentage identities when assessed by this method, such as at least about 75%, 80%, 85%, 90%, 95%, 98%, or 99% sequence identity to a molecule listed in Tables 1, 2, or 6.

When aligning short peptides (fewer than around 30 amino acids), the alignment is performed using the Blast 2 sequences function, employing the PAM30 matrix set to default parameters (open gap 9, extension gap 1 penalties). Proteins with even greater similarity to the reference sequence will show increasing percentage identities when assessed by this method, such as at least about 60%, 70%, 75%, 80%, 85%, 90%, 95%, 98%, 99% sequence identity to a molecule listed in Tables 1, 2, or 6. When less than the entire sequence is being compared for sequence identity, homologs will typically possess at least 75% sequence identity over short windows of 10-20 amino acids, and can possess sequence identities of at least 85%, 90%, 95% or 98% depending on their identity to the reference sequence. Methods for determining sequence identity over such short windows are described at the NCBI web site.

One indication that two nucleic acid molecules are closely related is that the two molecules hybridize to each other under stringent conditions, as described above. Nucleic acid sequences that do not show a high degree of identity may nevertheless encode identical or similar (conserved) amino acid sequences, due to the degeneracy of the genetic code. Changes in a nucleic acid sequence can be made using this degeneracy to produce multiple nucleic acid molecules that all encode substantially the same protein. Such homologous nucleic acid sequences can, for example, possess at least about 60%, 70%, 80%, 90%, 95%, 98%, or 99% sequence identity to a molecule listed in Tables 1, 2, or 6 determined by this method. An alternative (and not necessarily cumulative) indication that two nucleic acid sequences are substantially identical is that the polypeptide which the first nucleic acid encodes is immunologically cross reactive with the polypeptide encoded by the second nucleic acid.

One of skill in the art will appreciate that the particular sequence identity ranges are provided for guidance only; it is possible that strongly significant homologs could be obtained that fall outside the ranges provided.

Specific binding agent: An agent that binds substantially or preferentially only to a defined target such as a protein, enzyme, polysaccharide, oligonucleotide, DNA, RNA, recombinant vector or a small molecule. In an example, a "specific binding agent" is capable of binding to at least one of the disclosed cancer survival factor-associated molecules (such as those listed in Tables 1, 2, or 6). In other examples, the specific binding agent is capable of binding to a downstream factor regulated by at least one of the disclosed cancer survival factor-associated molecules (such as those listed in Tables 1, 2, or 6). Thus, a nucleic acid-specific binding agent binds substantially only to the defined nucleic acid, such as RNA, or to a specific region within the nucleic acid. For example, a "specific binding agent" includes an antisense compound (such as an antisense oligonucleotide, siRNA, miRNA, shRNA or ribozyme) that binds substantially to a specified RNA.

A protein-specific binding agent binds substantially only the defined protein, or to a specific region within the protein. For example, a "specific binding agent" includes antibodies and other agents that bind substantially to a specified polypeptide. Antibodies can be monoclonal or polyclonal antibodies that are specific for the polypeptide, as well as immunologically effective portions ("fragments") thereof. The determination that a particular agent binds substantially only to a specific polypeptide may readily be made by using or adapting routine procedures. One suitable in vitro assay makes use of the Western blotting procedure (described in many standard texts, including Harlow and Lane, Using Antibodies: A Laboratory Manual, CSHL, New York, 1999).

Subject: Living multi-cellular vertebrate organism, a category that includes human and non-human mammals.

Survival: Time interval between date of diagnosis or first treatment (such as surgery or first chemotherapy) and a specified event, such as relapse, metastasis or death. Overall survival is the time interval between the date of diagnosis or first treatment and date of death or date of last follow up. Relapse-free survival is the time interval between the date of diagnosis or first treatment and date of a diagnosed relapse (such as a locoregional recurrence) or date of last follow up. Metastasis-free survival is the time interval between the date of diagnosis or first treatment and the date of diagnosis of a metastasis or date of last follow up.

Target sequence: A sequence of nucleotides located in a particular region in the human genome that corresponds to a desired sequence, such as a cancer survival factor-associated sequence. Target sequences can encode target proteins. The target can be for instance a coding sequence; it can also be the non-coding strand that corresponds to a coding sequence. Examples of target sequences include those sequences associated with cancer survival factor-associated factors, such as any of those listed in Table 1, 2, or 6.

Tumor: The product of neoplasia is a neoplasm (a tumor), which is an abnormal growth of tissue that results from excessive cell division. A tumor that does not metastasize is referred to as "benign." A tumor that invades the surrounding tissue and/or can metastasize is referred to as "malignant." Neoplasia is one example of a proliferative disorder.

Ubiquitin protein ligase E3A (UBE3A): A member of the family of E3 ubiquitin ligases containing a C-terminal HECT domain (also known as E6 activating protein (E6AP)). This protein accepts ubiquitin from an E2 ubiquitin conjugating enzyme and transfers the ubiquitin to a target substrate. UBE3A interacts with the human papilloma virus E6 protein and targets p53 for ubiquitination and degradation. Maternal inheritance of a UBE3A deletion causes Angelman syndrome.

Nucleic acid and protein sequences for UBE3A are publicly available. For example, GENBANK® Accession Nos.: NM_130839, NM_000462, NM_130838, and BC009271 disclose UBE3A nucleic acid sequences, and GENBANK® Accession Nos.: NP_570854, NP_000453, NP_570853, and AAH09271 disclose UBE3A protein sequences, all of which are incorporated by reference as provided by GENBANK® on Feb. 13, 2009.

In one example, UBE3A includes a full-length wild-type (or native) sequence, as well as UBE3A allelic variants that retain the ability to be expressed at increased levels in a tumor and/or modulate an activity of a tumor, such as metastatic potential. In certain examples, UBE3A has at least 80% sequence identity, for example at least 85%, 90%, 95%, or 98% sequence identity to a publicly available UBE3A sequence.

Upregulated or activation: When used in reference to the expression of a nucleic acid molecule, such as a gene, refers to any process which results in an increase in production of a gene product. A gene product can be RNA (such as mRNA, rRNA, tRNA, and structural RNA) or protein. Therefore, gene upregulation or activation includes processes that increase transcription of a gene or translation of mRNA.

Examples of processes that increase transcription include those that facilitate formation of a transcription initiation complex, those that increase transcription initiation rate, those that increase transcription elongation rate, those that increase processivity of transcription and those that relieve transcriptional repression (for example by blocking the binding of a transcriptional repressor). Gene upregulation can include inhibition of repression as well as stimulation of expression above an existing level. Examples of processes that increase translation include those that increase translational initiation, those that increase translational elongation and those that increase mRNA stability.

Gene upregulation includes any detectable increase in the production of a gene product. In certain examples, production of a gene product (such as those listed in Tables 1, 2, and 6) increases by at least 1.5-fold, such as at least 2-fold, at least 3-fold or at least 4-fold, as compared to a control (such an amount of gene expression in a normal cell). In one example, a control is a relative amount of gene expression in a biological sample, such as in a breast tissue biopsy obtained from a subject that does not have breast cancer, or a lung tissue biopsy obtained from a subject that does not have lung cancer.

Additional terms commonly used in molecular genetics can be found in Benjamin Lewin, Genes V, published by Oxford University Press, 1994 (ISBN 0-19-854287-9); Kendrew et al (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

II. Methods of Determining Prognosis of a Subject with a Tumor

Described herein is the identification of a metastasis gene signature for determining the prognosis of a subject with a tumor (for example a breast tumor or lung tumor). In some examples, determining the prognosis includes determining whether a tumor is malignant or benign. In other examples, determining the prognosis includes predicting the outcome (such as chance of survival) of the subject with a tumor. Thus, provided herein is a method of prognosing a subject with a tumor. The method includes detecting expression of five or more cancer survival factor-associated genes, wherein the cancer survival factor-associated genes include the genes disclosed in Tables 1, 2, and 6 (for example, ABCF1, CORO1C, DPP3, PREB, UBE3A, and PTDSS1), and comparing expression of the cancer survival factor-associated genes in the tumor sample to a control. In some embodiments, the method includes detecting expression of five or more (such as at least 5, at least 6, at least 10, at least 12, at least 20, at least 25, at least 30, at least 50, at least 60, at least 70, or more) cancer survival factor-associated genes. In some examples, the method includes detecting expression of all of the cancer survival factor-associated molecules in Table 1, all of the cancer survival factor-associated molecules in Table 2, or all of the cancer survival factor-associated molecules in Table 6.

In one example, the method includes detecting expression of cancer survival factor-associated molecules including ABCF1, CORO1C, DPP3, PREB, UBE3A, and PTDSS1. In some examples, the method includes detecting expression of a plurality of cancer survival factor-associated molecules in a tumor sample obtained from the subject, wherein the plurality of cancer survival factor-associated molecules consists essentially of or consists of ABCF1, CORO1C, DPP3, PREB, UBE3A, and PTDSS1. In some examples, housekeeping gene expression is also detected, such as 1 to 10, 1 to 5, or 1 to 2 housekeeping genes.

In some embodiments of the method, an alteration in expression of five or more cancer survival factor-associated genes in the tumor sample relative to the control indicates a poor prognosis. In particular examples, an increase in expression of five or more cancer survival factor-associated genes in the tumor sample selected from the group consisting of ABCF1, CORO1C, DPP3, PREB, UBE3A, and PTDSS1 relative to the control indicates a poor prognosis. For example, an increase in the expression of five or more (for example, all) of ABCF1, CORO1C, DPP3, PREB, UBE3A, and PTDSS1 relative to a normal control sample or reference value (or range of values) indicates a poor prognosis, such as a decreased chance of survival (for example decreased overall survival, relapse-free survival, or metastasis-free survival). In an example, a decreased chance of survival includes a survival time of equal to or less than 60 months, such as 50 months, 40 months, 30 months, 20 months, 12 months, 6 months, or 3 months from time of diagnosis or first treatment. In other examples, no significant change in expression of five or more cancer survival factor-associated genes in the tumor sample selected from the group consisting of ABCF1, CORO1C, DPP3, PREB, UBE3A, and PTDSS1 relative to the control indicates a good prognosis (such as increased chance of survival, for example increased overall survival, relapse-free survival, or metastasis-free survival). In a specific example, no significant change in expression of ABCF1, CORO1C, DPP3, PREB, UBE3A, and PTDSS1 relative to the control indicates a good prognosis (such as increased chance of survival, for example increased overall survival, relapse-free survival, or metastasis-free survival). In an example, an increased chance of survival includes a survival time of at least 60 months from time of diagnosis, such as 60 months, 80 months, 100 months, 120 months, 150 months, or more from time of diagnosis or first treatment.

Expression of the cancer survival factor-associated genes can be detected using any suitable means known in the art. For example, detection of gene expression can be accomplished by detecting nucleic acid molecules (such as RNA) using nucleic acid amplification methods (such as RT-PCR) or array analysis. Detection of gene expression can also be accomplished using immunoassays that detect proteins (such as ELISA, Western blot, or RIA assay). Additional methods of detecting gene expression are well known in the art and are described in greater detail below.

The alteration in expression of the cancer survival factor-associated genes can be any measurable increase or decrease in expression that is correlated with a poor prognosis. In some embodiments, the increase or decrease in expression is at least 1.5-fold, at least 2-fold, at least 2.5-fold, at least 3-fold, at least 4-fold, at least 5-fold, at least 7-fold or at least 10-fold relative to a control sample. In some examples, the increase or decrease in expression is about 1.3-fold to about 4-fold, such as about 1.5-fold to 3.5-fold relative to a control sample. The relative increase or decrease in expression level amongst the cancer survival factor-associated genes can vary within a tumor and can also vary between tumor samples.

Poor prognosis can refer to any negative clinical outcome, such as, but not limited to, a decrease in likelihood of survival (such as overall survival, relapse-free survival, or metastasis-free survival), a decrease in the time of survival (e.g., less than 5 years, or less than one year), presence of a malignant tumor, an increase in the severity of disease, a decrease in response to therapy, an increase in tumor recurrence, an increase in metastasis, or the like. In particular examples, a poor prognosis is a decreased chance of survival (for example, a survival time of equal to or less than 60 months, such as 50 months, 40 months, 30 months, 20 months, 12 months, 6 months or 3 months from time of diagnosis or first treatment).

The control can be any suitable control against which to compare expression of a cancer survival factor-associated gene in a tumor sample. In some embodiments, the control sample is non-tumor tissue. In some examples, the non-tumor tissue is obtained from the same subject, such as non-tumor tissue that is adjacent to the tumor. In other examples, the non-tumor tissue is obtained from a healthy control subject. In other embodiments, the control is a reference value or ranges of values. For example, the reference value can be derived from the average expression values obtained from a group of healthy control subjects or non-tumor tissue from a group of cancer patients.

In other embodiments of the method, an alteration in expression of five or more cancer survival factor-associated genes in the tumor sample relative to the control indicates a diagnosis of the subject with a malignant tumor. The method includes detecting expression of five or more cancer survival factor-associated genes, wherein the cancer survival factor-associated genes include the genes disclosed in Tables 1, 2, and 6 (for example, ABCF1, CORO1C, DPP3, PREB, UBE3A, and PTDSS1), and comparing expression of the cancer survival factor-associated genes in the tumor sample to a control. In some embodiments, the method includes detecting expression of five or more (such as at least 6, at least 10, at least 12, at least 20, at least 25, at least 30, at least 50, at least 60, at least 70, or more) cancer survival factor-associated genes. In one example, the method includes detecting expression of a plurality of cancer survival factor-associated genes in a tumor sample obtained from the subject, wherein the plurality of cancer survival factor-associated genes consists essentially of ABCF1, CORO1C, DPP3, PREB, UBE3A, and PTDSS1. In some examples, housekeeping gene expression is also detected, such as 1 to 10, 1 to 5, or 1 to 2 housekeeping genes.

In some examples, an alteration in expression of five or more cancer survival factor-associated genes in the tumor sample relative to the control indicates that the subject has a malignant tumor. In particular examples, an at least 1.3-fold increase in expression of five or more cancer survival factor-associated genes in the tumor sample selected from the group consisting of ABCF1, CORO1C, DPP3, PREB, UBE3A, and PTDSS1 relative to the control indicates a malignant tumor. In some examples, an at least 1.3-fold increase in expression of five or more of ABCF1, CORO1C, DPP3, PREB, UBE3A, and PTDSS1 in the tumor sample relative to the control indicates a malignant tumor. In other examples, no significant change in expression (such as no statistically significant change) of five or more cancer survival factor-associated genes in the tumor sample (for example, ABCF1, CORO1C, DPP3, PREB, UBE3A, and PTDSS1) relative to the control indicates a benign (e.g., non-malignant) tumor. In a specific example, no significant change (such as no statistically significant change) in expression of ABCF1, CORO1C, DPP3, PREB, UBE3A, and PTDSS1 relative to the control indicates a benign (e.g., non-malignant) tumor.

The disclosed methods can be used to determine the prognosis of a subject with a cancer. Examples of hematological cancers include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, and myelodysplasia.

Examples of solid cancers, such as sarcomas and carcinomas, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, sebaceous gland carcinoma, papillary carcinoma, papillary adenocarcinoma, medullary carcinoma, bronchogenic carcinoma, renal cell carcinoma, hepatoma, bile duct carcinoma, choriocarcinoma, Wilms' tumor, cervical cancer, testicular tumor, bladder carcinoma, and CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma).

In a particular example, cancer includes breast cancer or lung cancer (such as non-small cell lung cancer, for example, squamous cell carcinoma or adenocarcinoma of the lung). In further examples, cancer includes prostate cancer, colorectal cancer, or ovarian cancer.

III. Detecting Expression of Cancer Survival Factor-Associated Genes

As described below, expression of five or more cancer survival factor-associated genes can be detected using any one of a number of methods well known in the art. Although exemplary methods are provided, the disclosure is not limited to such methods. Expression of either mRNA or protein is contemplated herein.

The disclosure includes isolated nucleic acid molecules that include specified lengths of a cancer survival factor-associated molecule nucleotide sequence, such as those genes listed in Tables 1, 2, and 6. Such molecules can include at least 10, at least 15, at least 20, at least 25, at least 30, at least 35, at least 40, at least 45, at least 50, or more consecutive nucleotides of these sequences or more, and can be obtained from any region of a cancer survival factor-associated molecule. In some examples, particular oligonucleotides and oligonucleotide analogs can include linear sequences up to about 200 nucleotides in length, for example a sequence (such as DNA or RNA) that is at least 6 nucleotides, for example at least 8, at least 10, at least 15, at least 20, at least 21, at least 25, at least 30, at least 35, at least 40, at least 45, at least 50, at least 100, or even at least 200 nucleotides long, or from about 6 to about 50 nucleotides, for example about 10-25 nucleotides, such as 12, 15, or 20 nucleotides. In one example, an oligonucleotide is a short sequence of nucleotides of at least one of the disclosed cancer survival factor-associated molecules listed in Tables 1, 2, or 6.

In some examples, the cancer survival factor associated molecules (such as those listed in Tables 1, 2, or 6) are detected utilizing an oligonucleotide probe. Such probes include short sequence of nucleotides, such as at least 8, at least 10, at least 15, at least 20, at least 21, at least 25, or at least 30 nucleotides in length, used to detect the presence of a complementary sequence by molecular hybridization.

A. Methods for Detection of mRNA

Gene expression can be evaluated by detecting mRNA encoding the gene of interest. Thus, the disclosed methods can include evaluating mRNA encoding five or more of the genes disclosed in Table 1, Table 2, or Table 6. In particular examples, mRNA encoding ABCF1, CORO1C, DPP3, PREB, UBE3A, and PTDSS1 is detected. In some examples, the mRNA is quantitated.

RNA can be isolated from a sample of a tumor (for example, a breast tumor or lung tumor) from a subject, a sample of adjacent non-tumor tissue from the subject, a sample of tumor-free tissue from a normal (healthy) subject, or combinations thereof, using methods well known to one skilled in the art, including commercially available kits. General methods for mRNA extraction are well known in the art and are disclosed in standard textbooks of molecular biology, including Ausubel et al., Current Protocols of Molecular Biology, John Wiley and Sons (1997). Methods for RNA extraction from paraffin embedded tissues are disclosed, for example, in Rupp and Locker, *Biotechniques* 6:56-60 (1988), and De Andres et al., *Biotechniques* 18:42-44 (1995). In one example, RNA isolation can be performed using purification kit, buffer set and protease from commercial manufacturers, such as QIAGEN® (Valencia, Calif.), according to the manufacturer's instructions. For example, total RNA from cells in culture (such as those obtained from a subject) can be isolated using QIAGEN® RNeasy® mini-columns. Other commercially available RNA isolation kits include MASTERPURE® Complete DNA and RNA Purification Kit (EPICENTRE® Madison, Wis.), and Paraffin Block RNA Isolation Kit (Ambion, Inc.). Total RNA from tissue samples can be isolated using RNA Stat-60 (Tel-Test). RNA prepared from tumor or other biological sample can be isolated, for example, by cesium chloride density gradient centrifugation.

Methods of gene expression profiling include methods based on hybridization analysis of polynucleotides, methods based on sequencing of polynucleotides, and proteomics-based methods. In some examples, mRNA expression in a sample is quantified using Northern blotting or in situ hybridization (Parker & Barnes, *Methods in Molecular Biology* 106:247-283, 1999); RNAse protection assays (Hod, *Biotechniques* 13:852-4, 1992); and PCR-based methods, such as reverse transcription polymerase chain reaction (RT-PCR) (Weis et al., *Trends in Genetics* 8:263-4, 1992). Alternatively, antibodies can be employed that can recognize specific duplexes, including DNA duplexes, RNA duplexes, and DNA-RNA hybrid duplexes or DNA-protein duplexes. Representative methods for sequencing-based gene expression analysis include Serial Analysis of Gene Expression (SAGE), and gene expression analysis by massively parallel signature sequencing (MPSS). In one example, RT-PCR can be used to compare mRNA levels in different samples, in normal and tumor tissues, with or without drug treatment, to characterize patterns of gene expression, to discriminate between closely related mRNAs, and to analyze RNA structure.

Methods for quantitating mRNA are well known in the art. In some examples, the method utilizes RT-PCR. For example, extracted RNA can be reverse-transcribed using a Gene-Amp® RNA PCR kit (Perkin Elmer, Calif., USA), following the manufacturer's instructions.

For example, TaqMan® RT-PCR can be performed using commercially available equipment. The system can include a thermocycler, laser, charge-coupled device (CCD) camera, and computer. The system amplifies samples in a 96-well format on a thermocycler. During amplification, laser-induced fluorescent signal is collected in real-time through fiber optics cables for all 96 wells, and detected at the CCD. The system includes software for running the instrument and for analyzing the data.

To minimize errors and the effect of sample-to-sample variation, RT-PCR can be performed using an internal standard. The ideal internal standard is expressed at a constant level among different tissues, and is unaffected by an experimental treatment. RNAs commonly used to normalize patterns of gene expression are mRNAs for the housekeeping genes GAPDH, β-actin, and 18S ribosomal RNA.

A variation of RT-PCR is real time quantitative RT-PCR, which measures PCR product accumulation through a dual-labeled fluorogenic probe (e.g., TAQMAN® probe). Real time PCR is compatible both with quantitative competitive PCR, where internal competitor for each target sequence is used for normalization, and with quantitative comparative PCR using a normalization gene contained within the sample, or a housekeeping gene for RT-PCR (see Heid et al., *Genome Research* 6:986-994, 1996). Quantitative PCR is also described in U.S. Pat. No. 5,538,848. Related probes and quantitative amplification procedures are described in U.S. Pat. No. 5,716,784 and U.S. Pat. No. 5,723,591. Instruments for carrying out quantitative PCR in microtiter plates are available from PE Applied Biosystems (Foster City, Calif.).

The steps of a representative protocol for quantitating gene expression using fixed, paraffin-embedded tissues as the RNA source, including mRNA isolation, purification, primer extension and amplification are given in various published journal articles (see Godfrey et al., *J. Mol. Diag.* 2:84 91, 2000; Specht et al., *Am. J. Pathol.* 158:419-29, 2001). Briefly, a representative process starts with cutting about 10 μm thick sections of paraffin-embedded tumor tissue samples or adjacent non-cancerous tissue. The RNA is then extracted, and protein and DNA are removed. Alternatively, RNA is isolated directly from a tumor sample or other tissue sample. After analysis of the RNA concentration, RNA repair and/or amplification steps can be included, if necessary, and RNA is reverse transcribed using gene specific promoters followed by RT-PCR.

The primers used for the amplification are selected so as to amplify a unique segment of the gene of interest (such as mRNA encoding ABCF1, CORO1C, DPP3, PREB, UBE3A, and/or PTDSS1). In some embodiments, expression of other genes is also detected, such as the genes listed in Table 1 and Table 6. Primers that can be used to amplify ABCF1, CORO1C, DPP3, PREB, UBE3A, and PTDSS1 are commercially available or can be designed and synthesized according to well known methods.

An alternative quantitative nucleic acid amplification procedure is described in U.S. Pat. No. 5,219,727. In this procedure, the amount of a target sequence in a sample is determined by simultaneously amplifying the target sequence and an internal standard nucleic acid segment. The amount of amplified DNA from each segment is determined and compared to a standard curve to determine the amount of the target nucleic acid segment that was present in the sample prior to amplification.

In some examples, gene expression is identified or confirmed using the microarray technique. Thus, the expression profile can be measured in either fresh or paraffin-embedded tumor tissue, using microarray technology. In this method, cancer survival factor-associated gene nucleic acid sequences of interest (including cDNAs and oligonucleotides) are plated, or arrayed, on a microchip substrate. The arrayed sequences are then hybridized with isolated nucleic acids (such as cDNA or mRNA) from cells or tissues of interest. Just as in the RT-PCR method, the source of mRNA typically is total RNA isolated from human tumors, and optionally from corresponding noncancerous tissue and normal tissues or cell lines.

In a specific embodiment of the microarray technique, PCR amplified inserts of cDNA clones are applied to a substrate in a dense array. In some examples, the array includes probes specific to at least five of the cancer survival factor-associated genes (such as those in Tables 1, 2, and 6). In some examples, probes specific for five or more of ABCF1, CORO1C, DPP3, PREB, UBE3A, and PTDSS1 nucleotide sequences are applied to the substrate, and the array can consist essentially of, or consist of these sequences. The micro arrayed nucleic acids are suitable for hybridization under stringent conditions. Fluorescently labeled cDNA probes may be generated through incorporation of fluorescent nucleotides by reverse transcription of RNA extracted from tissues of interest. Labeled cDNA probes applied to the chip hybridize with specificity to each spot of DNA on the array. After stringent washing to remove non-specifically bound probes, the chip is scanned by confocal laser microscopy or by another detection method, such as a CCD camera. Quantitation of hybridization of each arrayed element allows for assessment of corresponding mRNA abundance. With dual color fluorescence, separately labeled cDNA probes generated from two sources of RNA are hybridized pairwise to the array. The relative abundance of the transcripts from the two sources corresponding to each specified gene is thus determined simultaneously. The miniaturized scale of the hybridization affords a convenient and rapid evaluation of the expression pattern for cancer survival factor-associated genes, such as those in Tables 1, 2, and 6 (for example, ABCF1, CORO1C, DPP3, PREB, UBE3A, and PTDSS1). Microarray analysis can be performed by commercially available equipment, following manufacturer's protocols, such as are supplied with Affymetrix GeneChip® technology (Affymetrix, Santa Clara, Calif.), or Agilent's microarray technology (Agilent Technologies, Santa Clara, Calif.).

Serial analysis of gene expression (SAGE) is another method that allows the simultaneous and quantitative analysis of a large number of gene transcripts, without the need of providing an individual hybridization probe for each transcript. First, a short sequence tag (about 10-14 base pairs) is generated that contains sufficient information to uniquely identify a transcript, provided that the tag is obtained from a unique position within each transcript. Then, many transcripts are linked together to form long serial molecules, that can be sequenced, revealing the identity of the multiple tags simultaneously. The expression pattern of any population of transcripts can be quantitatively evaluated by determining the abundance of individual tags, and identifying the gene corresponding to each tag (see, for example, Velculescu et al., *Science* 270:484-7, 1995; and Velculescu et al., *Cell* 88:243-51, 1997).

In situ hybridization (ISH) is another method for detecting and comparing expression of genes of interest. ISH applies and extrapolates the technology of nucleic acid hybridization to the single cell level, and, in combination with the art of cytochemistry, immunocytochemistry and immunohistochemistry, permits the maintenance of morphology and the identification of cellular markers to be maintained and identified, and allows the localization of sequences to specific cells within populations, such as tissues and blood samples. ISH is a type of hybridization that uses a complementary nucleic acid to localize one or more specific nucleic acid sequences in a portion or section of tissue (in situ), or, if the tissue is small enough, in the entire tissue (whole mount ISH). RNA ISH can be used to assay expression patterns in a tissue, such as the expression of cancer survival factor-associated genes.

Sample cells or tissues are treated to increase their permeability to allow a probe, such as a cancer survival factor-associated gene-specific probe, to enter the cells. The probe is added to the treated cells, allowed to hybridize at pertinent temperature, and excess probe is washed away. A complementary probe is labeled so that the probe's location and quantity in the tissue can be determined, for example, using autoradiography, fluorescence microscopy or immunoassay. The sample may be any sample as herein described, such as a non-tumor sample or a breast or lung tumor sample. Since the sequences of the cancer survival factor-associated genes of interest are known, probes can be designed accordingly such that the probes specifically bind the gene of interest.

In situ PCR is the PCR-based amplification of the target nucleic acid sequences prior to ISH. For detection of RNA, an intracellular reverse transcription step is introduced to generate complementary DNA from RNA templates prior to in situ PCR. This enables detection of low copy RNA sequences.

Prior to in situ PCR, cells or tissue samples are fixed and permeabilized to preserve morphology and permit access of the PCR reagents to the intracellular sequences to be amplified. PCR amplification of target sequences is next performed either in intact cells held in suspension or directly in cytocentrifuge preparations or tissue sections on glass slides. In the former approach, fixed cells suspended in the PCR reaction mixture are thermally cycled using conventional thermal cyclers. After PCR, the cells are cytocentrifuged onto glass slides with visualization of intracellular PCR products by ISH or immunohistochemistry. In situ PCR on glass slides is performed by overlaying the samples with the PCR mixture under a coverslip which is then sealed to prevent evaporation of the reaction mixture. Thermal cycling is achieved by placing the glass slides either directly on top of the heating block of a conventional or specially designed thermal cycler or by using thermal cycling ovens.

Detection of intracellular PCR products is generally achieved by one of two different techniques, indirect in situ PCR by ISH with PCR-product specific probes, or direct in situ PCR without ISH through direct detection of labeled nucleotides (such as digoxigenin-11-dUTP, fluorescein-dUTP, $^3$H-CTP or biotin-16-dUTP), which have been incorporated into the PCR products during thermal cycling.

In some embodiments of the detection methods, the expression of one or more "housekeeping" genes or "internal controls" can also be evaluated. These terms include any constitutively or globally expressed gene (or protein, as discussed below) whose presence enables an assessment of cancer survival factor-associated gene (or protein) levels. Such an assessment includes a determination of the overall constitutive level of gene transcription and a control for variations in RNA (or protein) recovery.

B. Arrays for Profiling Cancer Survival Factor-Associated Gene Expression

In particular embodiments provided herein, arrays can be used to evaluate cancer survival factor-associated gene expression, for example to prognose or diagnose a patient with cancer (for example, breast or lung cancer). When describing an array that consists essentially of probes or primers specific for the genes listed in Table 1, Table 2, or Table 6, such an array includes probes or primers specific for these cancer survival factor-associated genes, and can further include control probes (for example to confirm the incubation conditions are sufficient). In some examples, the array may consist essentially of probes or primers specific for ABCF1, CORO1C, DPP3, PREB, UBE3A, and/or PTDSS1, and can further include one or more control probes. In some examples, the array may further include additional, such as about 5, 10, 20, 30, 40, 50, 60, or 70 additional cancer survival factor-associated genes. In other examples, the array may include fewer, such as 1, 2, 3, or 4 fewer cancer survival factor-associated genes. Exemplary control probes include GAPDH, β-actin, and 18S RNA. In one example, an array is a multi-well plate (e.g., 96 or 384 well plate).

In one example, the array includes, consists essentially of, or consists of probes or primers (such as an oligonucleotide or antibody) that can recognize ABCF1, CORO1C, DPP3, PREB, UBE3A, and PTDSS1. The oligonucleotide probes or primers can further include one or more detectable labels, to permit detection of hybridization signals between the probe and target sequence (such as one of the cancer survival factor-associated genes disclosed herein).

1. Array Substrates

The solid support of the array can be formed from an organic polymer. Suitable materials for the solid support include, but are not limited to: polypropylene, polyethylene, polybutylene, polyisobutylene, polybutadiene, polyisoprene, polyvinylpyrrolidine, polytetrafluoroethylene, polyvinylidene difluoroide, polyfluoroethylene-propylene, polyethylenevinyl alcohol, polymethylpentene, polycholorotrifluoroethylene, polysulfornes, hydroxylated biaxially oriented polypropylene, aminated biaxially oriented polypropylene, thiolated biaxially oriented polypropylene, ethyleneacrylic acid, thylene methacrylic acid, and blends of copolymers thereof (see U.S. Pat. No. 5,985,567).

In general, suitable characteristics of the material that can be used to form the solid support surface include: being amenable to surface activation such that upon activation, the surface of the support is capable of covalently attaching a biomolecule such as an oligonucleotide thereto; amenability to "in situ" synthesis of biomolecules; being chemically inert such that at the areas on the support not occupied by the oligonucleotides or proteins (such as antibodies) are not amenable to non-specific binding, or when non-specific binding occurs, such materials can be readily removed from the surface without removing the oligonucleotides or proteins (such as antibodies).

In another example, a surface activated organic polymer is used as the solid support surface. One example of a surface activated organic polymer is a polypropylene material aminated via radio frequency plasma discharge. Other reactive groups can also be used, such as carboxylated, hydroxylated, thiolated, or active ester groups.

2. Array Formats

A wide variety of array formats can be employed in accordance with the present disclosure. One example includes a linear array of oligonucleotide bands, generally referred to in the art as a dipstick. Another suitable format includes a two-dimensional pattern of discrete cells (such as 4096 squares in a 64 by 64 array). As is appreciated by those skilled in the art, other array formats including, but not limited to slot (rectangular) and circular arrays are equally suitable for use (see U.S. Pat. No. 5,981,185). In some examples, the array is a multi-well plate. In one example, the array is formed on a polymer medium, which is a thread, membrane or film. An example of an organic polymer medium is a polypropylene sheet having a thickness on the order of about 1 mil. (0.001 inch) to about 20 mil., although the thickness of the film is not critical and can be varied over a fairly broad range. The array can include biaxially oriented polypropylene (BOPP) films, which in addition to their durability, exhibit low background fluorescence.

The array formats of the present disclosure can be included in a variety of different types of formats. A "format" includes any format to which the solid support can be affixed, such as microtiter plates (e.g., multi-well plates), test tubes, inorganic sheets, dipsticks, and the like. For example, when the solid support is a polypropylene thread, one or more polypropylene threads can be affixed to a plastic dipstick-type device; polypropylene membranes can be affixed to glass slides. The particular format is, in and of itself, unimportant. All that is necessary is that the solid support can be affixed thereto without affecting the functional behavior of the solid support or any biopolymer absorbed thereon, and that the format (such as the dipstick or slide) is stable to any materials into which the device is introduced (such as clinical samples and hybridization solutions).

The arrays of the present disclosure can be prepared by a variety of approaches. In one example, oligonucleotide or protein sequences are synthesized separately and then attached to a solid support (see U.S. Pat. No. 6,013,789). In another example, sequences are synthesized directly onto the support to provide the desired array (see U.S. Pat. No. 5,554,501). Suitable methods for covalently coupling oligonucleotides and proteins to a solid support and for directly synthesizing the oligonucleotides or proteins onto the support are known to those working in the field; a summary of suitable methods can be found in Matson et al., *Anal. Biochem.* 217: 306-10, 1994. In one example, the oligonucleotides are synthesized onto the support using conventional chemical techniques for preparing oligonucleotides on solid supports (such as PCT applications WO 85/01051 and WO 89/10977, or U.S. Pat. No. 5,554,501).

A suitable array can be produced using automated means to synthesize oligonucleotides in the cells of the array by laying down the precursors for the four bases in a predetermined pattern. Briefly, a multiple-channel automated chemical delivery system is employed to create oligonucleotide probe populations in parallel rows (corresponding in number to the number of channels in the delivery system) across the substrate. Following completion of oligonucleotide synthesis in a first direction, the substrate can then be rotated by 90° to permit synthesis to proceed within a second set of rows that are now perpendicular to the first set. This process creates a multiple-channel array whose intersection generates a plurality of discrete cells.

The oligonucleotides can be bound to the polypropylene support by either the 3' end of the oligonucleotide or by the 5' end of the oligonucleotide. In one example, the oligonucleotides are bound to the solid support by the 3' end. However, one of skill in the art can determine whether the use of the 3' end or the 5' end of the oligonucleotide is suitable for bonding to the solid support. In general, the internal complementarity of an oligonucleotide probe in the region of the 3' end and the 5' end determines binding to the support.

In particular examples, the oligonucleotide probes on the array include one or more labels, that permit detection of oligonucleotide probe:target sequence hybridization complexes.

C. Detecting Cancer Survival Factor-Associated Proteins

In some examples, expression of five or more proteins encoded by the genes disclosed in Table 1, Table 2, or Table 6 is analyzed. In particular examples, ABCF1, CORO1C, DPP3, PREB, UBE3A, and PTDSS1 proteins are analyzed. Suitable biological samples include samples containing protein obtained from a tumor (such as a breast tumor or lung tumor) of a subject, from non-tumor tissue of the subject, and/or protein obtained from one or more samples of cancer-free subjects. Detecting an alteration in the amount of five or more proteins encoded by the genes in Table 1, Table 2, or Table 6 (such as ABCF1, CORO1C, DPP3, PREB, UBE3A, or PTDSS1) in a tumor from the subject relative to a control, such as an increase or decrease in expression, indicates the prognosis or diagnosis of the subject, as described above.

Antibodies specific for the disclosed proteins (for example, ABCF1, CORO1C, DPP3, PREB, UBE3A, and PTDSS1) can be used for detection and quantitation of cancer survival factor-associated proteins by one of a number of immunoassay methods that are well known in the art, such as those presented in Harlow and Lane (*Antibodies, A Laboratory Manual*, CSHL, New York, 1988). Methods of constructing such antibodies are known in the art. In addition, such antibodies may be commercially available.

Exemplary commercially available antibodies include ABCF1 antibodies (such as catalog number ab50976, Abcam, Cambridge, Mass.; catalog numbers H00000023-B01 and H00000023-A01, Abnova, Walnut, Calif.; catalog number sc-81047, Santa Cruz Biotechnology, Santa Cruz, Calif.), CORO1C antibodies (such as catalog number ab15719, Abcam,; catalog numbers H00023603-M02 and H00023603-A01, Abnova; catalog number sc-32211, Santa Cruz Biotechnology), DPP3 antibodies (such as catalog numbers ab56107, ab56108, and ab56109, Abcam; catalog numbers H00010072-B03 and H00010072-M01A, Abnova; catalog number sc-55640, Santa Cruz Biotechnology), PREB antibodies (such as catalog number ab42501, Abcam, Cambridge, Mass.; catalog 113-A01, Abnova), UBE3A antibodies (such as catalog numbers ab3519 and ab58266, Abcam; catalog numbers H00007337-M01 and H00007337-MO2, Abnova; catalog number sc-100614, Santa Cruz Biotechnology), and PTDSS1 antibodies (such as catalog number ab69951, Abcam; catalog number H00009791-P01, Abnova; catalog number sc-51410, Santa Cruz Biotechnology).

Any standard immunoassay format (such as ELISA, Western blot, or RIA assay) can be used to measure protein levels. Thus, in one example, polypeptide levels of five or more of ABCF1, CORO1C, DPP3, PREB, UBE3A, and PTDSS1 in a tumor (for example, a breast or lung tumor) can readily be evaluated using these methods. Immunohistochemical techniques can also be utilized for cancer survival factor-associated gene detection and quantification. General guidance regarding such techniques can be found in Bancroft and Stevens (*Theory and Practice of Histological Techniques*, Churchill Livingstone, 1982) and Ausubel et al. (*Current Protocols in Molecular Biology*, John Wiley & Sons, New York, 1998).

For the purposes of quantitating cancer survival factor-associated proteins, a biological sample of the subject that includes cellular proteins can be used. Quantitation of proteins (for example ABCF1, CORO1C, DPP3, PREB, UBE3A, and/or PTDSS1) can be achieved by immunoassay. The amount of cancer survival factor-associated proteins can be assessed in the tumor and optionally in the adjacent non-tumor tissue or in tissue from cancer-free subjects. The amounts of cancer survival factor-associated protein in the tumor can be compared to levels of the protein found in cells from a cancer-free subject or other control (such as a standard value or reference value). A significant increase or decrease in the amount can be evaluated using statistical methods known in the art.

Quantitative spectroscopic methods, such as SELDI, can be used to analyze cancer survival factor-associated protein expression in a sample (such as tumor tissue, non-cancerous tissue, and tissue from a cancer-free subject). In one example, surface-enhanced laser desorption-ionization time-of-flight (SELDI-TOF) mass spectrometry is used to detect protein expression, for example by using the ProteinChip™ (Ciphergen Biosystems, Palo Alto, Calif.). Such methods are well known in the art (for example see U.S. Pat. No. 5,719,060; U.S. Pat. No. 6,897,072; and U.S. Pat. No. 6,881,586). SELDI is a solid phase method for desorption in which the analyte is presented to the energy stream on a surface that enhances analyte capture or desorption.

Therefore, in a particular example, the chromatographic surface includes antibodies that specifically bind ABCF1, CORO1C, DPP3, PREB, UBE3A, and PTDSS1. In other examples, the chromatographic surface consists essentially of, or consists of, antibodies that specifically bind ABCF1, CORO1C, DPP3, PREB, UBE3A, and PTDSS1. In some examples, the chromatographic surface includes antibodies that bind other molecules, such as housekeeping proteins (e.g., β-actin or myosin).

In another example, antibodies are immobilized onto the surface using a bacterial Fc binding support. The chromatographic surface is incubated with a sample, such as a sample of a tumor. The antigens present in the sample can recognize the antibodies on the chromatographic surface. The unbound proteins and mass spectrometric interfering compounds are washed away and the proteins that are retained on the chromatographic surface are analyzed and detected by SELDI-TOF. The MS profile from the sample can be then compared using differential protein expression mapping, whereby relative expression levels of proteins at specific molecular weights are compared by a variety of statistical techniques and bioinformatic software systems.

IV. Application of a Gene Signature for Treatment of Cancer

It is disclosed herein that expression of the genes disclosed in Tables 1, 2, and 6 herein correlate with clinical outcome of cancer patients (such as breast cancer or lung cancer patients). In a particular example, detecting an increase in expression or activity of five or more of (such as all of) ABCF1, CORO1C, DPP3, PREB, UBE3A, and PTDSS1 indicates a poor prognosis and/or diagnosis of a malignant tumor.

A. Methods of Treatment

Provided herein is a method of treating cancer (for example, breast or lung cancer) in a subject, including administering to the subject a therapeutically effective amount of an agent that alters (increases or decreases) expression or activity of at least one cancer survival factor-associated molecule of Tables 1, 2, or 6, for example, ABCF1, CORO1C, DPP3, PREB, UBE3A, or PTDSS1. In particular examples, the agent decreases expression of ABCF1, CORO1C, DPP3, PREB, UBE3A, or PTDSS1. Such agents can alter the expression of nucleic acid sequences (such as DNA, cDNA, or mRNAs) or proteins. In other examples, the agent decreases the biological activity of ABCF1, CORO1C, DPP3, PREB, UBE3A, or PTDSS1. An alteration in the expression or activity can be any detectable increase or decrease that results in a biological effect. For example, an agent can increase or decrease the expression or activity by a desired amount, for example by at least about 1.5-fold, at least about 2-fold, at least about 2.5-fold, at least about 3-fold, at least about 4-fold, at least about 5-fold, at least about 7-fold, or at least about 10-fold relative to activity or expression in a control (for example the relative amount of expression in the absence of treatment).

Treatment of cancer by altering the expression or activity of one or more of the disclosed cancer survival factor-associated genes (such as decreasing the expression or activity of one or more of ABCF1, CORO1C, DPP3, PREB, UBE3A, or PTDSS1) can include delaying the development of the tumor in a subject (such as preventing metastasis of a tumor). Treatment of a tumor also includes reducing signs or symptoms associated with the presence of such a tumor (for example by reducing the size or volume of the tumor or a metastasis thereof). Such reduced growth can in some examples decrease or slow metastasis of the tumor, or reduce the size or volume of the tumor by at least 10%, at least 20%, at least 50%, or at least 75%. In some examples, treatment of cancer by altering the expression or activity of one or more of the disclosed cancer survival factor-associated genes (such as ABCF1, CORO1C, DPP3, PREB, UBE3A, or PTDSS1) can include increasing survival, for example, overall survival, relapse-free survival, or metastasis-free survival, such as increased survival time compared to in the absence of treatment. Such increased survival can include e.g., survival time of at least about 50 months from time of diagnosis, such as about 60 months, about 80 months, about 100 months, about 120 months or about 150 months from time of diagnosis or first treatment.

In some embodiments, a subject is screened to determine if they would benefit from treatment with an agent that alters (increases or decreases) expression or activity of at least one cancer survival factor-associated molecule, for example, ABCF1, CORO1C, DPP3, PREB, UBE3A, or PTDSS1. In some examples, expression of at least one cancer survival factor-associated molecule (such as ABCF1, CORO1C, DPP3, PREB, UBE3A, or PTDSS1) is determined in a sample from the subject. If the expression of at least one cancer survival factor-associated is altered (for example increased or decreased) relative to a control sample, the subject may be treated with an agent that alters (increases or decreases) expression or activity of the at least one cancer survival factor-associated molecule. In other examples, expression of at least one cancer survival factor-associated molecule (such as ABCF1, CORO1C, DPP3, PREB, UBE3A, or PTDSS1) is determined in a sample from the subject, and if the expression of at least one cancer survival factor-associated molecule is altered, the subject is determined to have a malignant tumor and may be treated with an agent that alters (increases or decreases) expression or activity of the at least one cancer survival factor-associated molecule.

In some embodiments, the agent is a specific binding agent, such as an antibody, antisense compound or small molecule inhibitor, that decreases the activity or expression of a target gene. Methods of preparing antibodies against a specific target protein are well known in the art. A cancer survival factor-associated protein or a fragment or conservative variant thereof can be used to produce antibodies which are immunoreactive or specifically bind to an epitope of the cancer survival factor-associated protein. Polyclonal antibodies, antibodies which consist essentially of pooled monoclonal antibodies with different epitopic specificities, as well as distinct monoclonal antibody preparations are included. The preparation of polyclonal antibodies is well known to those skilled in the art. See, for example, Green et al., "Production of Polyclonal Antisera," in: *Immunochemical Protocols*, pages 1-5, Manson, ed., Humana Press, 1992; Coligan et al., "Production of Polyclonal Antisera in Rabbits, Rats, Mice and Hamsters," in: *Current Protocols in Immunology*, section 2.4.1, 1992. The preparation of monoclonal antibodies likewise is conventional (see, for example, Kohler & Milstein, *Nature* 256:495, 1975; Coligan et al., sections 2.5.1-2.6.7;

and Harlow et al. in: *Antibodies: a Laboratory Manual*, page 726, Cold Spring Harbor Pub., 1988).

Any type of antisense compound that specifically targets and regulates expression of target nucleic acid (such as a disclosed cancer survival factor-associated gene or downstream target thereof) is contemplated for use. An antisense compound is one which specifically hybridizes with and modulates expression of a target nucleic acid molecule (such as a cancer survival associated factor, for example, those disclosed in Tables 1, 2, or 6). In some examples, the agent is an antisense compound selected from an antisense oligonucleotide, a siRNA, a miRNA, a shRNA or a ribozyme. As such, these compounds can be introduced as single-stranded, double-stranded, circular, branched or hairpin compounds and can contain structural elements such as internal or terminal bulges or loops. Double-stranded antisense compounds can be two strands hybridized to form double-stranded compounds or a single strand with sufficient self complementarity to allow for hybridization and formation of a fully or partially double-stranded compound.

In some examples, an antisense oligonucleotide is a single stranded antisense compound, such that when the antisense oligonucleotide hybridizes to a target mRNA, the duplex is recognized by RNaseH, resulting in cleavage of the mRNA. In other examples, a miRNA is a single-stranded RNA molecule of about 21-23 nucleotides that is at least partially complementary to an mRNA molecule that regulates gene expression through an RNAi pathway. In further examples, a shRNA is an RNA oligonucleotide that forms a tight hairpin, which is cleaved into siRNA. siRNA molecules are generally about 20-25 nucleotides in length and may have a two nucleotide overhang on the 3' ends, or may be blunt ended. Generally, one strand of a siRNA is at least partially complementary to a target nucleic acid. Methods of designing, preparing and using antisense compounds are within the abilities of one of skill in the art. Furthermore, sequences for the disclosed cancer survival factor-associated genes are publicly available.

Antisense compounds specifically targeting a cancer survival factor-associated gene (or other target nucleic acid), such as those provided in Tables 1, 2, and 6, can be prepared by designing compounds that are complementary to the target nucleotide sequence, such as a mRNA sequence. Antisense compounds need not be 100% complementary to the target nucleic acid molecule to specifically hybridize and regulate expression the target gene. For example, the antisense compound, or antisense strand of the compound if a double-stranded compound, can be at least 75%, at least 80%, at least 85%, at least 90%, at least 95%, at least 99% or 100% complementary to the selected target nucleic acid sequence (such as the nucleic acid sequences associated with the GenBank accession numbers provided above in Section I). Methods of screening antisense compounds for specificity are well known in the art (see, for example, U.S. Pre-Grant Publication No. 2003-0228689).

B. Therapeutic Agents

Therapeutic agents are agents that when administered in therapeutically effective amounts induce the desired response (e.g., treatment of a breast or lung tumor). In one example, therapeutic agents are specific binding agents that bind with higher affinity to a molecule of interest, than to other molecules. For example, a specific binding agent can be one that binds with high affinity to one or more cancer survival factor-associated genes, or a downstream factor that is regulated by one or more of the disclosed cancer survival factor-associated genes, but does not substantially bind to another gene or gene product. For example, the agent can interfere with gene expression (transcription, processing, translation, post-translational modification), such as, by interfering with the gene's mRNA and blocking translation of the gene product or by post-translational modification of a gene product, or by causing changes in intracellular localization. In another example, a specific binding agent binds to a protein encoded by one or more cancer survival factor-associated genes, or a downstream target of a cancer survival factor-associated gene, with a binding affinity in the range of 0.1 to 20 nM and reduces or inhibits the activity of such protein.

Contemplated herein is the use of specific binding agents to decrease expression or activity of one or more cancer survival factor-associated genes whose up-regulation is correlated with a poor prognosis, such as decreasing expression or activity of one or more genes shown in Tables 1, 2, and 6 (for example, ABCF1, CORO1C, DPP3, PREB, UBE3A, or PTDSS1).

Examples of specific binding agents include antisense compounds (such as antisense oligonucleotides, siRNAs, miRNAs, shRNAs and ribozymes), antibodies, ligands, recombinant proteins, peptide mimetics, and soluble receptor fragments. Methods of making antisense compounds that can be used clinically are known in the art. In addition, antisense compounds may be commercially available.

Exemplary commercially available antisense compounds include ABCF1 antisense compounds (such as catalog number H00000023-R03, Abnova, Walnut, Calif.; catalog numbers sc-95478 and sc-95478-SH, Santa Cruz Biotechnology, Santa Cruz, Calif.), CORO1C antisense compounds (such as catalog number H00023603-R01, Abnova; catalog numbers sc-44693 and sc-44693-SH, Santa Cruz Biotechnology), DPP3 antisense compounds (such as catalog numbers sc-62230 and sc-62230-SH, Santa Cruz Biotechnology), PREB antisense compounds (such as catalog number H00010113-R01), UBE3A antisense compounds (such as catalog numbers H00007337-R01, -R02, and -R03, Abnova; catalog numbers sc-43742 and sc-43742-SH, Santa Cruz Biotechnology), and PTDSS1 antisense compounds (such as catalog numbers sc-72365 and sc-72365-SH, Santa Cruz Biotechnology).

Further examples of specific binding agents include antibodies. Methods of making antibodies that can be used clinically are known in the art. In addition, antibodies may be commercially available, such as those discussed above.

Specific binding agents can be therapeutic, for example by altering the biological activity of a cancer survival factor-associated nucleic acid or protein, or a nucleic acid or protein that is negatively regulated by a cancer survival factor-associated gene. For example, a specific binding agent that binds with high affinity to a cancer survival factor-associated gene, or a downstream target of a cancer survival factor-associated gene, may substantially reduce the biological function of the gene or gene product. In other examples, a specific binding agent that binds with high affinity to one of the proteins encoded by a cancer survival factor-associated gene, or a downstream target of a cancer survival factor-associated gene, may substantially reduce the biological function of the protein. Such agents can be administered in therapeutically effective amounts to subjects in need thereof, such as a subject having cancer.

C. Administration of Therapeutic Agents

Therapeutic agents can be administered to a subject in need of treatment using any suitable means known in the art. Methods of administration include, but are not limited to, intradermal, intramuscular, intraperitoneal, parenteral, intravenous, subcutaneous, vaginal, rectal, intranasal, inhalation, oral, or by gene gun. Intranasal administration refers to delivery of the compositions into the nose and nasal passages through one or both of the nares and can include delivery by a spraying mechanism or droplet mechanism, or through aerosolization of the therapeutic agent.

Administration of the compositions by inhalant can be through the nose or mouth via delivery by spraying or droplet mechanisms. Delivery can be directly to any area of the respiratory system via intubation. Parenteral administration is generally achieved by injection. Injectables can be prepared in conventional forms, either as liquid solutions or suspensions, solid forms suitable for solution of suspension in liquid prior to injection, or as emulsions. Injection solutions and suspensions can be prepared from sterile powders, granules, and tablets. Administration can be systemic or local.

Therapeutic agents can be administered in any suitable manner, preferably with pharmaceutically acceptable carriers. Pharmaceutically acceptable carriers are determined in part by the particular composition being administered, as well as by the particular method used to administer the composition. Accordingly, there is a wide variety of suitable formulations of pharmaceutical compositions of the present disclosure. The pharmaceutically acceptable carriers (vehicles) useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of one or more therapeutic agents Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Administration can be accomplished by single or multiple doses. The dose required will vary from subject to subject depending on the species, age, weight and general condition of the subject, the particular therapeutic agent being used and its mode of administration. In some examples, the dose of antisense compound (such as siRNA, shRNA, or miRNA) is about 1 mg to about 1000 mg, about 10 mg to about 500 mg, or about 50 mg to about 100 mg. In some examples, the dose of antisense compound is about 1 mg, about 10 mg, about 50 mg, about 100 mg, about 250 mg, about 500 mg or about 1000 mg. In some embodiments, the dose of antisense compound is about 1.0 mg/kg to about 100 mg/kg, or about 5.0 mg/kg to about 500 mg/kg, about 10 mg/kg to about 100 mg/kg, or about 25 to about 50 mg/kg. In some examples, the dose of antisense compound is about 1.0 mg/kg, about 5 mg/kg, about 10 mg/kg, about 12.5 mg/kg, about 15 mg/kg, about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg or about 100 mg/kg. In some embodiments, the dose of antibody is about 1 mg/kg to about 25 mg/kg, such as about 2 mg/kg to about 15 mg/kg, about 2 mg/kg to about 10 mg/kg, or about 2 mg/kg to about 8 mg/kg. In some examples, the dose of antibody is about 1 mg/kg, about 2 mg/kg, about 4 mg/kg, about 5 mg/kg, about 6 mg/kg, about 8 mg/kg, about 10 mg/kg, about 15 mg/kg, about 20 mg/kg, or about 25 mg/kg. In other embodiments, the dose of antibody is about 50 mg/m$^2$ to about 500 mg/m$^2$, such as about 50 mg/m$^2$ to about 400 mg/m$^2$, about 100 mg/m$^2$ to about 400 mg/m$^2$, or about 250 mg/m$^2$ to about 400 mg/m$^2$. In some examples, the dose is about 50 mg/m$^2$, about 100 mg/m$^2$, about 150 mg/m$^2$, about 200 mg/m$^2$, about 250 mg/m$^2$, about 300 mg/m$^2$, about 400 mg/m$^2$, or about 500 mg/m$^2$. It will be appreciated that these dosages are examples only, and an appropriate dose can be determined by one of ordinary skill in the art using only routine experimentation.

The disclosed specific binding agents may be used in combination with additional cancer treatments (such as surgery, radiation therapy, and/or chemotherapy). In one example, the additional therapy includes one or more anti-tumor pharmaceutical treatments which can include radiotherapeutic agents, anti-neoplastic chemotherapeutic agents, antibiotics, alkylating agents and antioxidants, kinase inhibitors, and other agents. Particular examples of additional therapeutic agents that can be used include microtubule binding agents (such as paclitaxel, docetaxel, vinblastine, vindesine, vinorelbine (navelbine), the epothilones, colchicine, dolastatin 15, nocodazole, podophyllotoxin, rhizoxin, and derivatives and analogs thereof), DNA intercalators or cross-linkers (such as cisplatin, carboplatin, oxaliplatin, mitomycins, such as mitomycin C, bleomycin, chlorambucil, cyclophosphamide, and derivatives and analogs thereof), DNA synthesis inhibitors (such as methotrexate, 5-fluoro-5'-deoxyuridine, 5-fluorouracil and analogs thereof), DNA and/or RNA transcription inhibitors (such as actinomycin D, daunorubicin, doxorubicin and derivatives and analogs thereof), antibodies (such as trastuzumab, bevacizumab, cetuximab, panitumumab), enzymes, enzyme inhibitors (such as camptothecin, etoposide, formestane, trichostatin and derivatives and analogs thereof), kinase inhibitors (such as imatinib, gefitinib, and erolitinib), and gene regulators (such as raloxifene, 5-azacytidine, 5-aza-2'-deoxycytidine, tamoxifen, 4-hydroxytamoxifen, mifepristone and derivatives and analogs thereof). Methods and therapeutic dosages of such agents are known to those skilled in the art, and can be determined by a skilled clinician.

Other therapeutic agents, for example anti-tumor agents, that may or may not fall under one or more of the classifications above, also are suitable for administration in combination with the described specific binding agents. By way of example, such agents include doxorubicin, apigenin, zebularine, cimetidine, and derivatives and analogs thereof.

The disclosure is further illustrated by the following non-limiting Examples.

EXAMPLES

Example 1

Metastatic Gene Signatures in Breast Cancer

This example provides gene signatures predictive for metastasis in subjects with breast cancer.

Methods

Animal Models of Metastasis:

Murine breast adenocarcinoma 4T1 cells (American Type Culture Collection, Manassas, Va.) were harvested from cell culture flasks using trypsin-EDTA (Life Technologies, Inc., Grand Island, N.Y.), washed three times in HBSS, and adjusted to the appropriate final concentration. Cell preparations were kept on ice until injection.

To generate the liver metastases splenic vein model (LvMsv), BALB-c mice were anesthetized with isoflurane and prepared for surgery under sterile conditions. The animals were positioned in right lateral recumbency, shaved and wiped with 70% ethanol. A left subcostal incision, approximately 10 mm long, was made and the peritoneum was opened. The spleen was exposed and gently retracted; the gastrosplenic ligament and short gastric vessels were identified and divided, leading to complete mobility of the spleen on its hilar pedicle. The spleen was then extracorporealized and positioned on sterile saline soaked gauze. Next, cell suspension (200 μl; $1\times10^7$ cells/ml) was slowly injected into the upper splenic pole, using a 30-gauge needle (Becton Dickinson, Franklin Lakes, N.J.). After injection, the needle was slowly removed, and slight pressure was applied to the spleen to achieve hemostasis and minimize extra-splenic seeding. Five minutes were elapsed to allow portal vein embolization. Splenectomy by application of a medium Ligaclip (Ethicon Endo-Surgery Inc., Somerville, N.J.) to splenic vessels and sharp excision of the organ followed. The abdominal cavity was then closed with 9-mm wound autoclips (Roboz Surgical, Rockville, Md.). Animals were monitored and sacrificed when they became moribund. Livers were examined with 2× surgical loupes and hepatic metastases were immediately resected, snap frozen in liquid nitrogen, and ultimately stored at −80° C.

To generate the lung metastases tail vein model (LMtv), tail veins of female BALB-c mice were cannulated with a 27-gauge needle and 50 μl of 4T1 cell suspension ($5\times10^6$ cells/ml) was injected. After 14 days, they were sacrificed and the tracheobronchopulmonary tree was resected and insufflated with PBS. With the use of trans-illumination and 2× surgical loupes, the lung metastases were immediately resected, snap frozen in liquid nitrogen, and stored at −80° C.

To generate the spontaneous liver and lung metastases models (LvMsp and LMsp, respectively), 4T1 tumor cell suspension (100 μl; $5\times10^6$ cells/ml) was injected into the left cephalad mammary gland of BALB-c mice. After 14 days, the resultant orthotopic tumors were excised under sterile conditions, and the tumor was immediately snap frozen in liquid nitrogen and stored at −80° C. The wound was closed with autoclips. After an additional 14 days, animals were sacrificed and the spontaneous lung and liver metastases were procured, as described above.

RNA Preparation and Hybridization:

To minimize individual variation, tumor samples were used from three individual mice, from each metastatic animal model. Twenty cryostat sections (10 μm) were cut in all samples under RNase free conditions and stored at −80° C. Sections were stained with hematoxylin and eosin, and only tumor area was micro-dissected. Total RNA was immediately isolated using the PicoPure® RNA Isolation Kit (Arcturus, Mountain View, Calif.). Total RNA (30 ng) from each sample was used in the reverse transcription of two consecutive rounds of linear amplification, first using the MessageAmp™ II aRNA Amplification Kit, followed by biotin labeling using the MessageAmp™ II-Biotin Enhanced Kit (Ambion, Austin, Tex.). RNA concentrations were measured by Nano-Drop™ ND-1000 (NanoDrop, Wilmington, Del.). The quality of RNA preparations was assessed with Bioanalyzer RNA 6000 Nano LabChip Kit (Agilent Technology, Santa Clara, Calif.); the 28S/18S ribosomal RNA ratio was used as control. All samples included in this study had a 28S/18S ribosomal RNA ratio of more than 1.5, with an average of 2.0. Each biotinylated cRNAs (20 μg) was fragmented and hybridized to an Affymetrix® Mouse Genome 430A 2.0 Array GeneChip (Affymetrix, Santa Clara, Calif.), which comprised over 22,000 probe sets representing over 14,500 well-substantiated mouse genes. Arrays were scanned utilizing standard Affymetrix protocols. Image analysis and probe quantification was performed with the Affymetrix software (GCOS), which produced raw probe intensity data.

Statistical Analysis:

Expression profiles were generated for independent biological triplicates of each tumor group to minimize individual variation and ensure reliability of the data. Raw intensity profiles were analyzed, using Partek Genomics Suite Software (Partek Inc., St. Louis, Mo.), to perform microarray normalization and statistical analysis. Robust Microarray Analysis (RMA) was applied for microarray normalization. The latest Affymetrix arrays annotation files (April 2008) were downloaded from Affymetrix web site and used for all further analysis. Significantly regulated genes were defined as those genes from one experimental group whose expression was statistically significantly different from another group by virtue of multi-way ANOVA. Resulted ratios were transformed into log 2 values and used as expression levels for genes in metastatic gene signatures. Genes included in the lists were further selected with a false discovery rate (FDR) of less than 10%. Each probe set was treated as a separate gene, whereby averaging of the triplicate led to the defined data of the respective gene.

Selection of Metastasis Gene Signatures:

The spontaneous metastasis gene signature (SpMGS), containing 79 genes, was generated by identifying genes common to LMsp and LvMsp, and absent from LMtv, LvMsv, and LR-associated genes. Similarly, the embolic metastasis gene signature (EMGS), containing 32 genes, was generated by identifying genes common to LMtv and LvMsv, and absent from LMsp, LvMsp, and LR. Comparing the two signatures gave preliminary validation to the theory and method.

Gene Ontology Analysis:

To interpret the biological significance of the signature genes, a gene ontology analysis was conducted using Ingenuity Pathway Analysis software (IPA, version 6.0; Ingenuity Systems, Redwood City, Calif.). Each Affymetrix probe identifier was mapped to its corresponding gene in the Ingenuity Pathways Knowledge Base. This functional database allows the correlation of genes, biochemical pathways, cells, diseases, drugs and other biological variables. Using the software, the signature genes were categorized based on location, cellular components, and molecular and biologic functions. It was also used to facilitate the calculation of gene data enrichment relative to functions greater than expected by chance.

The significance of gene enrichment of biological function was derived from a p-value (p<0.05).

Results

Figure 2:
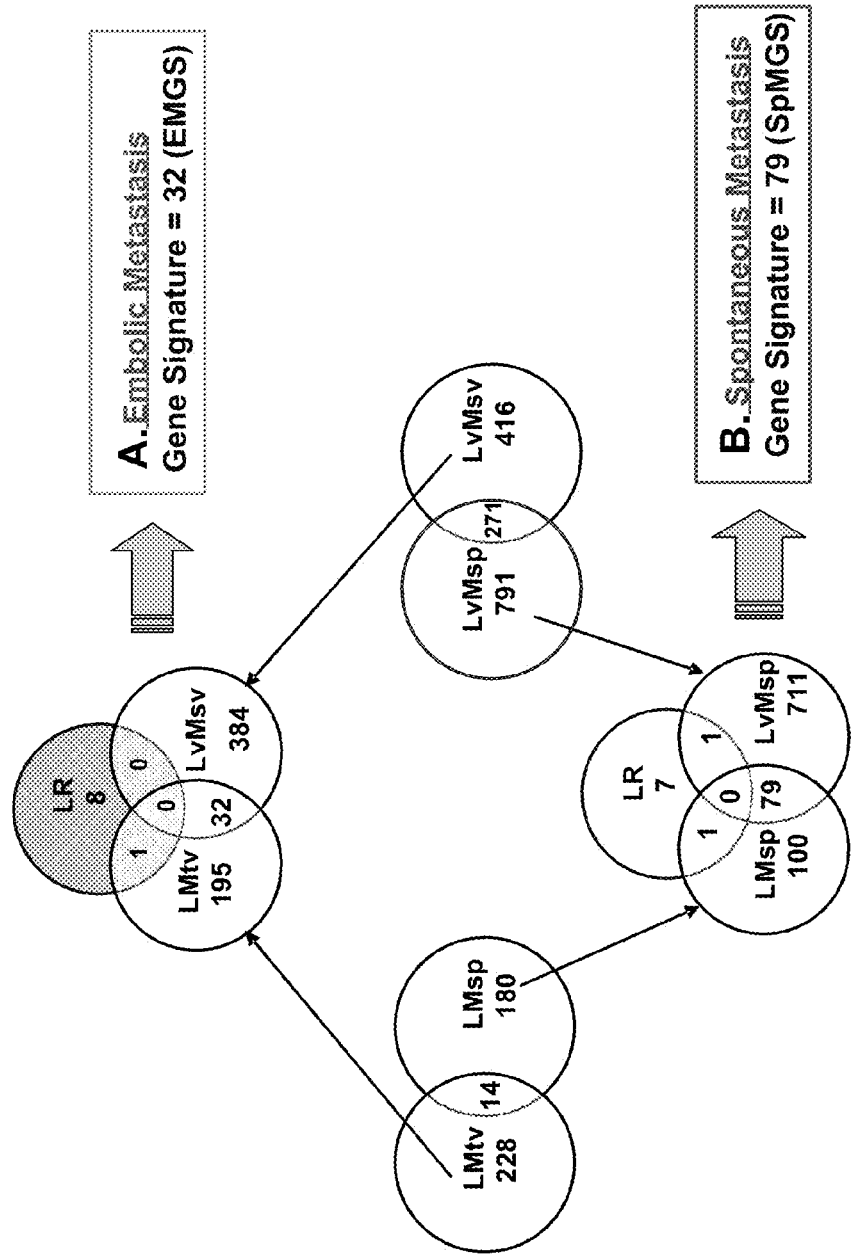
FIG. 2 is a series of Venn diagrams showing derivation of embolic metastasis gene signature (EMGS) and spontaneous metastasis gene signature (SpMGS) gene sets.

Mouse models of embolic and spontaneous metastasis were generated as described above (FIG. 1). Genes that were statistically and significantly differentially expressed between the metastatic tumor types (spontaneous and embolic) and primary tumor were identified. As shown in FIG. 2, 194 unique genes (corresponding to 226 gene probe sets) were associated with LMsp; 1062 unique genes (corresponding to 1203 gene probe sets) were associated with LvMsp; 242 unique genes (corresponding to 271 gene probes sets) were associated with LMtv; 687 unique genes (corresponding to 788 gene probe sets) were associated with LvMsv; only 9 unique genes were associated with local recurrence (LR).

The embolic lesions served as a control for the ambient changes in gene expression associated with tumor growth in a given parenchyma, despite the need for the earlier steps in metastatic competency. Using Venn logic the ambient changes were excluded and the alternate expression patterns were targeted as a source for predictive power. Spontaneous metastasis gene signature (SpMGS) containing 79 genes (Table 1) and embolic metastasis gene signature (EMGS) containing 32 genes (Table 2) were generated.

TABLE 1

Mouse genes identified as spontaneous metastasis gene signature

| Gene Symbol | Gene name |
| --- | --- |
| 1810010G06Rik (Atp2c2) | ATPase, Calcium transporting, type 2C, member 2 |
| 2010106G01Rik (Sppl2a) | Signal peptide peptidase-like 2A |
| 2310044D20Rik (Fam174a) | Family with sequence similarity 174, member A |
| 2610304G08Rik (Rprd1b) | Regulation of nuclear pre-mRNA domain containing 1B |
| 2900002H16Rik (Rilpl1) | Rab interacting lysosomal protein-like 1 |
| 5730536A07Rik (Fam96a) | Family with sequence similarity 96, member A |
| 6230421P05Rik (Bach1) | BTB and CSC homology 1 |
| AA536749 (Mprip) | Myosin phosphatase Rho interacting protein |
| Abcf1 | ATP-binding cassette, sub-family F, member1 |
| Acat2/Acat3 | Acetyl-Coenzyme A acetyltransferase 2/Acetyl-Coenzyme A acetyltransferase 3 |
| Anapc5 | Anaphase-promoting complex subunit 5 |
| Arf6 | ADP-ribosylation factor 6 |
| Arhgap6 | Rho GTPase activating protein 6 |
| Arl6ip6 | ADP-ribosylation factor-like 6 interacting protein 6 |
| Atp5a1 | ATP synthase H+ transporting, mitochondrial F1 complex, alpha subunit, isoform 1 |
| Atp6v0c | ATPase, H+ transporting, lysosomal V0 subunit C |
| Atp6v1c1 | ATPase, H+ transporting, lysosomal V1 subunit C, isoform 1 |
| BC019943 | cDNA sequence BC019943 |
| BC025462 | Fanconi anemia, complementation group I, mRNA with apparent retained intron |
| Cklfsf7 (Cmtm7) | CKLF-like MARVEL transmembrane domain containing 7 |
| Coro1c | Coronin, actin binding protein, 1C |
| D10Ertd610e (Geft) | DNA segment, Chr. 10, ERATO Doi 610, expressed |
| D10Wsu52e (HSPC117) | DNA segment, Chr. 10, Wayne State University 52, expressed |
| D6Ertd109e (Etfl) | DNA segment, Chr 6, ERATO Doi 109, expressed |
| Ddx20 | DEAD (Asp-Glu-Ala-Asp) box polypeptide 20 |
| Defcr15 | Defensin related cryptdin 15 |
| Diap1 | Diaphanous homolog 1 (*Drosophila*) |
| Dnahc11 | Dynein, axonemal, heavy chain 11 |

TABLE 1-continued

Mouse genes identified as spontaneous metastasis gene signature

| Gene Symbol | Gene name |
| --- | --- |
| Dock7 | Dedicator of cytokinesis 7 |
| Dpp3 | Dipeptidyl-peptidase 3 |
| Eif2s3x | Eukaryotic translation initiation factor 2, subunit 3, structural gene X-linked |
| Eif3s2 (Eif3i) | Eukaryotic translation initiation factor 3, subunit 2 beta |
| Fbxw11 | F-box and WD-40 domain protein 11 |
| Fos | FBJ osteosarcoma oncogene |
| Gdap10 | Ganglioside-induced differentiation-associated-protein 10 |
| Gem | GTP binding protein (gene overexpressed in skeletal muscle) |
| Hcrt | Hypocretin |
| Hspa9a | Heat shock protein 9 |
| Ikbkb | Inhibitor of kappa B kinase beta |
| Il11 | Interleukin 11 |
| Inpp5e | Inositol polyphosphate-5-phosphatase E |
| Lgtn | Ligatin |
| Lrig1 | Leucine-rich repeats and immunoglobulin-like domains 1 |
| Maf1 | MAF1 homolog (*S. cerevisiae*) |
| Map3k7 | Mitogen-activated protein kinase kinase kinase 7 |
| Mll3 | Myeloid/lymphoid or mixed-lineage leukemia 3 |
| Mpa2 (Gbp4)/ LOC547126 | Guanylate binding protein 4 |
| Mrpl41 | Mitochondrial ribosomal protein L41 |
| Mtfr1 | Mitochondrial fission regulator 1 |
| Nedd4 | Neural precursor cell expressed, developmentally down-regulated 4 |
| Papola | Poly (A) polymerase alpha |
| Pbef1 (Nampt) | Nicotinamide phosphoribosyltransferase |
| Pms2 | Postmeiotic segregation increased 2 (*S. cerevisiae*) |
| Ppp2r2d | Protein phosphatase 2, regulatory subunit B, delta isoform |
| Preb | Prolactin regulatory element binding |
| Ptdss1 | Phosphatidylserine synthase 1 |
| Pvr | Poliovirus receptor |
| Rab31 | RAB31, member RAS oncogene family |
| Rest | RE1-silencing transcription factor |
| Samd11 | Sterile alpha motif domain containing 11 |
| Serhl | Serine hydrolase-like |
| Sfrs2ip | Splicing factor, arginine/serine-rich 2, interacting protein |
| Slc19a1 | Solute carrier family 19 (sodium/hydrogen exchanger), member 1 |
| Snrpn | Small nuclear ribonucleoprotein N |
| Sntb2 | Syntrophin, basic 2 |
| Sorcs3 | Sortilin-related VPS10 domain containing receptor 3 |
| Sox4 | SRY-box containing gene 4 |
| Sprr2j | Small proline-rich protein 2J |
| Stam2 | Signal transducing adaptor molecule (SH3 domain and ITAM motif) 2 |
| Stx5a | Syntaxin 5A |
| Thrap3 | Thyroid hormone receptor associated protein 3 |
| Tob2 | Transducer of ERBB2, 2 |
| Tufm | Tu translation elongation factor, mitochondrial |
| Ubc | Ubiquitin C |
| Ube2e1 | Ubiquitin-conjugating enzyme E2E 1, UBC4/5 homolog (yeast) |
| Ube3a | Ubiquitin protein ligase E3A |
| Usp7 | Ubiquitin specific peptidase 7 |
| V1rd2 | Vomeronasal 1 receptor, D2 |
| Xbp1 | X-box binding protein 1 |

TABLE 2

Mouse genes identified as embolic metastasis gene signature

| Gene Symbol | Gene Name |
| --- | --- |
| 2810003C17Rik (Aif1l/C9orf58) | Allograft inflammatory factor 1-like |

TABLE 2-continued

Mouse genes identified as embolic metastasis gene signature

| Gene Symbol | Gene Name |
|---|---|
| 6720467C03Rik (Fam92a) | Family with sequence similarity 92, member A |
| Adamts15 | A disintegrin-like and metallopeptidase (reprolysin type) with thrombospondin type 1 motif, 15 |
| Adrb1 | Adrenergic receptor, beta 1 |
| Akap12 | A kinase (PRKA) anchor protein (gravin) 12 |
| Ap3b1 | Adaptor-related protein complex 3, beta 1 subunit |
| Atp1b1 | ATPase, Na+/K+ transporting, beta 1 polypeptide |
| Bhlhb5 | Basic helix-loop-helix domain containing, class B5 |
| Cpxm2 | Carboxypeptidase X 2 (M14 family) |
| Cxcl12 | Chemokine (C-X-C motif) ligand 12 |
| Dpep1 | Dipeptidase 1 (renal) |
| Dsp | Desmoplakin |
| Eln | Elastin |
| Fcgr2b | Fc receptor, IgG, low affinity IIb |
| Folr2 | Folate receptor 2 (fetal) |
| Gkap1 | G kinase anchoring protein 1 |
| Gnai1 | Guanine nucleotide binding protein (G protein), alpha inhibiting 1 |
| Gucy1b3 | Guanylate cyclase 1, soluble, beta 3 |
| Heph | Hephaestin |
| Il4ra | Interleukin 4 receptor, alpha |
| Inmt | Indolethylamine N-methyltransferase |
| Klf15 | Kruppel-like factor 15 |
| Klhl13 | Kelch-like 13 (*Drosophila*) |
| Lum | Lumican |
| Mbd1 | Methyl-CpG binding domain protein 1 |
| Mylk | Myosin, light polypeptide kinase |
| Slc9a3r2 | Solute carrier family 9 (sodium/hydrogen exchanger), member 3 regulator 2 |
| Sox17 | SRY-box containing gene 17 |
| Sparcl1 | SPARC-like 1 |
| Tgfb1i1 | Transforming growth factor beta 1 induced transcript 1 |
| Tmem30b | Transmembrane protein 30B |
| Tsc22d3 | TSC22 domain family, member 3 |

An annotation study using Ingenuity Pathways Analysis software was performed to evaluate whether the SpMGS signature was enriched in genes that are coordinately involved in specific biological pathways or molecular and cellular functions. Among the 79 SpMGS genes, 67 genes mapped onto the Ingenuity network, 12 genes were unmapped, and 40 of the genes were eligible for functional or pathways analysis. Thirty genes were significantly enriched in molecular and cellular functions which classified into 24 categories. The overall annotation of the genes in the SpMGS is summarized in Table 3. The top functions were cellular development, cell death, cell morphology, gene expression, and RNA damage and repair.

TABLE 3

Functional classification of SpMGS by pathway analysis

| Molecular and Cell Function | No. | p-value | Gene Symbol |
|---|---|---|---|
| Cellular development | 9 | 7.19E-05-4.94E-02 | FOS, IKBKB, GEM, HCRT, M-RIP, MAP3K7, SLC19A1, GEFT, IL11 |
| Cell death | 8 | 6.56E-04-4.27E-02 | FOS, IKBKB, ARF6, MAP3K7, DPP3, NAMPT, STAM2, IL11 |
| Cell morphology | 8 | 9.96E-04-4.73E-02 | FOS, DIAPH1, ARF6, HCRT, ATP6V0C, M-RIP, GEM, REST |
| Cell to cell signaling and interaction | 7 | 9.96E-04-4.68E-02 | IKBKB, FOS, ARF6, DIAPH1, HCRT, SLC19A1, IL11 |
| Gene expression | 7 | 9.96E-04-4.68E-02 | IKBKB, FOS, MAP3K7, REST, ETF1, IL11, BACH1 |
| RNA damage and repair | 2 | 9.96E-04-9.96E-04 | FOS, MAP3K7 |
| RNA post-transcriptional modification | 3 | 9.96E-04-4.27E-02 | FOS, MAP3K7, DDX20 |
| Lipid metabolism | 4 | 1.19E-03-4.68E-02 | ARF6, ACAT2, HCRT, INPP5E |
| Molecular transport | 10 | 1.19E-03-4.68E-02 | FOS, IKBKB, ARF6, ATP6V0C, ACAT2, HCRT, ATP6V1C1, INPP5E, SLC19A1, NAMPT |
| Small molecule biochemistry | 7 | 1.19E-03-4.68E-02 | FOS, ARF6, ACAT2, HCRT, INPP5E, SLC19A1, NAMPT |
| Cell cycle | 2 | 4.35E-03-4.52E-02 | IKBKB, FOS |
| Cellular assembly and organization | 8 | 4.35E-03-4.68E-02 | CORO1C, ARF6, DIAPH1, M-RIP, REST, STX5, DDX20, GEFT |
| Cellular growth and proliferation | 3 | 4.35E-03-4.68E-02 | FOS, IKBKB, IL11 |
| DNA replication, recombination, and repair | 3 | 4.35E-03-4.27E-02 | FOS, PMS2 |
| Nucleic acid metabolism | 1 | 4.35E-03-2.16E-02 | SLC19A1 |
| Vitamin and mineral metabolism | 1 | 4.35E-03-3.43E-02 | SLC19A1 |
| Cellular function and maintenance | 7 | 7E-03-4.68E-02 | FOS, IKBKB, CORO1C, ARF6, DIAPH1, STX5, SLC19A1 |
| Cellular compromise | 2 | 8.68E-03-4.27E-02 | ATP6V0C, PMS2 |
| Drug metabolism | 3 | 8.68E-03-4.68E-02 | FOS, HCRT, SLC19A1 |
| Protein synthesis | 6 | 1.24E-02-3.67E-02 | EIF2S3, DPP3, ANAPC5, EIF3I, ABCF1, MRPL41 |
| Carbohydrate metabolism | 2 | 1.3E-02-3.43E-02 | FOS, NAMPT |
| Cellular movement | 2 | 1.73E-02-4.27E-02 | DIAPH1, GEM, IL11 |
| Amino acid metabolism | 2 | 2.58E-02-3.43E-02 | FOS, SLC19A1 |
| Cell signaling | 2 | 2.58E-02-4.42E-02 | IKBKB, MAP3K7 |

Example 2

Validation of Metastatic Gene Signatures in Human Breast Cancer Patients

This example provides validation of the metastatic gene signatures as predictive of survival in human breast cancer patients.

Methods

Application of Gene Signatures to Public Datasets:

To compare expression data from the mouse and human datasets a correspondence had to be made between probes on the mouse arrays with probes on the human arrays. Mouse signature gene symbols were matched to human gene symbols by using a mouse-human homology gene list provided by Microarray Data Base (mAdb, Center for Cancer Research, National Cancer Institute, National Institutes of Health). The gene symbol identifier was then used to match genes represented in different microarray datasets. For cDNA microarrays, genes with fluorescent hybridization signals at least 1.5-fold greater than the local background fluorescent signal in the reference channel (Cy3) were considered adequately measured and were selected for further analyses. For Affymetrix microarray data, signal intensity values were z-transformed into ratios, and genes with technically adequate measurements obtained from at least 90% of the samples in a given dataset were selected for analysis. Gene value was generated by the averaging of each probe set within a given experimental group. The patterns of expression in published datasets were subsequently analyzed according to the identified gene signature. Averaged linkage clustering was performed using Cluster Software. After application of each signature, the sample data from each public dataset was segregated into two classes based on the first bifurcation of its hierarchical dendrogram. This most proximal bifurcation represents the most fundamental surrogate of fidelity of the samples profile with the tested signature. Survival analysis was performed on each class that resulted from the grouping.

Published Datasets Used to Validate Gene Signature van de Vijver gene set:

This was a validation study of a predictive expression signature, which involved 295 young patients with early stage breast cancer, of which 151 were lymph node negative, 226 were estrogen receptor positive, and 110 had received adjuvant chemotherapy (van de Vijver et al., *N. Engl. J. Med.* 347:1999-2009, 2002).

GSE4922:

This was a derivation study for the molecular profiling of the histologic grading of breast cancer; the patients used are referred to as the Uppsala Cohort. Two hundred and forty nine of the 316 patients in the cohort were used to derive the molecular profile of which 211 were estrogen receptor-positive, 81 were lymph node positive, and 58 showed p53 mutation. Eighty six patients which overlapped with the GSE2990 dataset were excluded, leaving 163 patients in this analysis. These data were originally published by Bergh et al. (*Nature Med.* 1:1029-1034, 1995) and reinvestigated by Ivshina et al. (*Cancer Res.* 66:10292-10301, 2006).

GSE2034:

This was a derivation and validation analysis of a gene signature for the prediction of breast cancer patient outcomes. It consisted of 286 lymph node negative breast cancer patients who never received adjuvant chemotherapy and of which 209 were estrogen receptor positive (Wang et al., *Lancet* 365:671-679, 2005).

GSE1456:

This study was a derivation and validation analysis of a predictive gene signature for the outcomes of women with breast cancer. It involved 159 patients with breast cancer, of which 82% were estrogen receptor positive, 62% were lymph node negative and 79% were treated with adjuvant chemotherapy (Pawitan et al., *Breast Cancer Res.* 7:R953-R964, 2005).

GSE2990:

This study was a derivation and validation analysis of a correlative gene signature aimed at histologic grade. It involved 189 women with breast cancer of which 160 were lymph node negative. Sixty-four estrogen receptor positive samples were used to derive a signature that effectively differentiates outcomes and grade (Sotiriou et al., *J. Natl. Cancer Inst.* 98:262-272, 2006).

GSE7390:

This study was a multicenter validation trial, to evaluate the clinical utility of a gene signature for the management of early node negative breast cancer. The analysis involved 198 patients, of which 22 were excluded in the current analysis because of overlap with the GSE2990 dataset (Desmedt et al., *Clin. Cancer Res.* 13:3207-3214, 2007).

Clustering:

Hierarchical cluster analysis was carried out with Stanford University Cluster Software (Eisen et al., *Proc. Natl. Acad. Sci. USA* 95:14863-14868, 1998). The average linkage uncentered Pearson correlation was used as the similarity metric for clustering of both genes and arrays. The clusters were visualized using TreeView (available online from the Eisen Lab at Lawrence Berkeley National Laboratory).

Survival Analysis:

Kaplan Meier estimates and log rank testing were used to construct survival curves. Statistical significance was evaluated using Cox regression analysis of hazard ratios (HRs). Overall survival in the van de Vijver, GSE4922, and GSE7390 datasets were defined as the time interval between the first date of any form of treatment and the last follow-up date or date of death; patients alive at the date of last follow-up were censored at that date. Metastasis-free survival in the van de Vijver dataset was defined as the interval from the first treatment day to the day of the diagnosis of distant metastases. All other patients were censored on their date of last follow-up, including alive without disease, alive with locoregional recurrence, alive with a second primary cancer, and death from an alternate cause. For the GSE2034, GSE1456 and GSE2990 datasets, the relapse-free survival was defined as the time interval between the date of breast surgery and the date of a diagnosed relapse or last follow-up. Women who developed contralateral breast cancer were censored. The data reported herein were based on the 10-year survival calculation for the van de Vijver, GSE4922 and GSE2990 datasets, 5-year survival calculation for GSE2034 and GSE1456 datasets, and 12-year survival calculation for GSE7390 dataset. Patients with missing survival data or those that were reported to have zero follow-up time were excluded from survival analyses. In any specific analysis involving one or more clinical variables, a patient was excluded if the value of at least one variable was missing; resulting in slightly different numbers of patients in various analyses. All reported p-values are two-sided. Multivariate analysis by Cox proportional hazard regression and all survival statistics were done in Partek Genomics Suite.

Results

Three publicly available datasets were used to evaluate the prognostic value of the metastatic gene signatures. These datasets included the van de Vijver, GSE4922, and GSE2034 gene sets. Forty-eight of the SpMGS genes were mapped to the van de Vijver dataset, 49 were mapped to the GSE4922 dataset, and 51 were mapped to the GSE2034 dataset. Patients with incomplete clinical annotations or follow-up were excluded from analysis.

To facilitate visualization and identify subgroups of patients that expressed the SpMGS, the gene expression patterns and samples were organized using hierarchical clustering. The patients segregated into two classes, assignment of which was based on whether they expressed the gene signature. More specifically, they were defined by the first bifurcation in the hierarchical clustering dendrogram. To correlate clinical outcome, the probability of remaining free of distant metastases and overall survival was calculated given the genetic expression class for each signature.

In the van de Vijver dataset, Kaplan Meier curves showed a significant association between the SpMGS and both overall and metastasis-free survival (p<0.0005) in 10-year survival analysis. This analysis indicated that the risk of metastasis was significantly higher for patients in Class 2 than Class 1. Class 1 had better overall survival and metastases-free survival [(94% and 85%, respectively, at 5 years), (84% and 76%, respectively, at 10 years)] compared with class 2 [(77% and 64%, respectively, at 5 years), (63% and 51%, respectively, at 10 years)] (FIG. 3A). The univariate hazard ratio (HR) was 0.36 (p<0.00003) for metastasis and 0.33 (p=0.00014) for death. Multivariable proportional-hazards analysis confirmed that the SpMGS classification was a significant independent factor in predicting disease outcome (p=0.003). The SpMGS was a sensitive predictor of distant metastases, with HR of 0.46 (Table 4).

TABLE 4

Multivariable proportional-hazards analysis of risk of distant metastasis as first event in van de Vijver dataset

|  | HR | p-value |
|---|---|---|
| SpMGS | 0.46 | 0.003 |
| Primary tumor size (≤2 cm vs. >2 cm) | 0.62 | 0.03 |
| Node (negative vs. positive) | 0.79 | 0.45 |
| Age (<45 years vs. ≥45 years) | 2.05 | 0.0009 |
| Chemotherapy exposure (no vs. yes) | 1.54 | 0.17 |
| Estrogen receptor status (negative vs. positive) | 1.1 | 0.69 |
| Differentiation: intermediate vs. well | 2.15 | 0.03 |
| poorly vs. well | 2.8 | 0.004 |

A univariate Cox proportional-hazards model was used to evaluate the association of the signatures with clinical outcome in each category, stratified for multiple clinical parameters. As summarized in Table 5, the prognostic profile based on SpMGS was accurate in predicting the outcome of disease. Comparing patients in Class 1 with those in Class 2, revealed a hazard ratio (HR) for distant metastases of 0.43 for lymph-node negative patients and 0.28 for lymph-node positive patients (p<0.05 for both). Similarly, the prognostic profile was strongly associated with disease outcome in groups of patients with tumor diameter less than or equal 20 mm [HR=0.33, (p=0.002)] and tumor diameter greater than 20 mm [HR=0.45, (p=0.02)], as well as in patients with age less than or equal to 45 years [HR=0.30, (p=0.00007)] and age greater than 45 years [HR=0.46, (p=0.05)]. Furthermore, the SpMGS could be used to stratify tumors of well and intermediate differentiation into good and poor prognostic subcategories [HR 0.24 and 0.26, respectively (p<0.05)], but was less correlative with the stratification of poorly differentiated lesions (p=0.67). The clinical corollary was significant for tumors that were estrogen receptor positive [HR=0.36, (p<0.05)], but not for those that were estrogen receptor negative. This analysis also showed that SpMGS was a strong predictor of improved outcomes in the group of patients who did or did not receive chemotherapy [HR=0.25 and 0.43, respectively (p<0.05), by log-rank test)].

TABLE 5

Univariate Cox proportional-hazards model for metastasis-free survival according to SpMGS and EMGS in van de Vijver dataset

|  | HR | p-value | Total patients |
|---|---|---|---|
| Node positive | 0.28 | 0.0009 | 144 |
| Node negative | 0.43 | 0.006 | 151 |
| Tumor size ≤2 cm | 0.33 | 0.002 | 150 |
| Tumor size >2 cm | 0.45 | 0.02 | 140 |
| Age ≤45 years | 0.3 | 0.00007 | 166 |
| Age >45 years | 0.46 | 0.05 | 129 |
| Chemotherapy: yes | 0.25 | 0.002 | 110 |
| Chemotherapy: no | 0.43 | 0.003 | 185 |
| Estrogen receptor positive | 0.36 | 0.0003 | 226 |
| Estrogen receptor negative | 0.75 | 0.63 | 69 |
| Differentiation: Poor | 0.87 | 0.67 | 119 |
| Intermediate | 0.24 | 0.0008 | 101 |
| Well | 0.26 | 0.03 | 75 |

Class 1 vs. class 2 hazard ratio

Figure 3B:
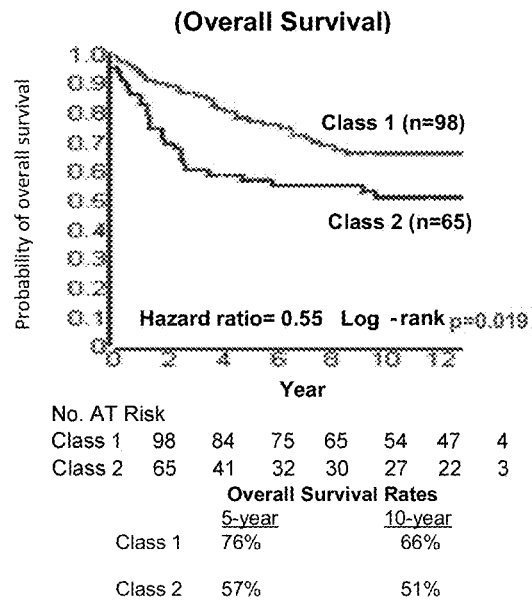
FIG. 3B is a Kaplan-Meier plot of overall survival of patients expressing SpMGS in the GSE4922 dataset. Patients who exhibited the SpMGS signature were assigned class 2, whereas those who did not were assigned class 1.
Figure 3C:
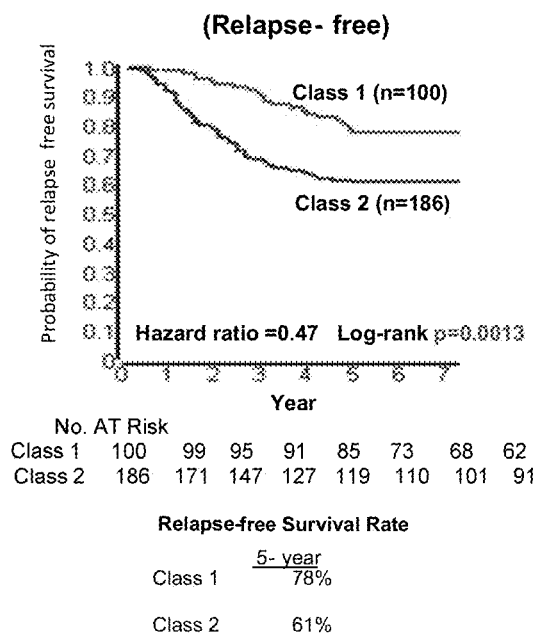
FIG. 3C is a Kaplan-Meier plot of relapse-free survival of patients expressing SpMGS in the GSE2034 dataset. Patients who exhibited the SpMGS signature were assigned class 2, whereas those who did not were assigned class 1.

A similar analysis was performed on both GSE4922 and GSE2034 datasets. Information on overall survival in GSE4922 dataset and metastasis-free survival in GSE2034 dataset were provided in the database. The survival analysis showed that the risk of metastasis or death was significantly higher among patients with an expression profile associated with SpMGS Class 2 [HR 0.55 (p=0.019) and 0.47 (p=0.0013), respectively] (FIGS. 3B and 3C).

When similar analysis was done using the 32-gene EMGS on the three data sets, the predictive outcomes were either statistically insignificant or not as powerful as the SpMGS (FIGS. 4A-C). However, the EMGS signature was statistically significantly associated with overall survival in the GSE4922 dataset (p=0.03; FIG. 4B) and with relapse-free survival in the GSE2034 dataset (p=0.04; FIG. 4C).

To determine if SpMGS is unique from previously published work, the SpMGS was cross referenced to other human breast cancer gene profiles. SpMGS has only one gene in common (PTDSS1) with the 70 gene signature by van't Veer et al. (*Nature* 415:530-536, 2002; MammaPrint® signature), one gene in common (FOS) with the 264-gene signature by Ivshina et al. (*Cancer Res.* 66:10292-12301, 2006), and one gene in common (TOB2) with the 186-gene signature of Liu et al. (*N. Engl. J. Med.* 356:217-226, 2007). Together these results indicated that the mouse-derived SpMGS was an independent new expression profile that had prognostic value when applied to human disease.

Example 3

Identification of a Six-Gene Prognostic Signature for Breast Cancer

This example describes evaluation of the prognostic value of the individual genes in the SpMGS and EMGS signatures, and identification of a six-gene signature associated with breast cancer prognosis.

Methods

To further evaluate the prognostic value of each gene within the signatures, inter-cohort multivariate Cox proportional-hazards analysis of each signature gene was performed. Six genes of SpMGS were predictive in all three datasets (van de Vijver, GSE4922, and GSE2034). Survival analysis was performed on the 3 original public datasets described in Example 1 (van de Vijver, GSE4922 and GSE2034) utilizing the 6-gene model. Additionally, the 6-gene model was tested against three additional independent public datasets (GSE1456, GSE2990, GSE7390; described in Example 2).

Results

To further evaluate the prognostic value of each gene within the signatures, multivariate Cox proportional-hazards analysis of each signature gene was performed in different datasets based on clinical information. Genes significantly correlated with patient outcomes (p<0.05) were determined for each data sets. Only genes with p<0.05 and present in at least one of three data sets were selected. Among the three data sets, a total of 17 unique genes were derived from the original 79 SpMGS genes (Table 6). Further, 12 of these 17 (70.6%) SpMGS genes had a hazard ratio of greater than 1 (indicating that up-regulation of those genes will lead to poor prognosis), of which 6 genes were predictive in all three datasets. This served as the logic and derivation of the 6-gene model. In contrast, 5 of the 17 genes had a hazard ratio of less than 1, indicating that down-regulation of those genes will lead to poor prognosis. Sixteen of 32 genes from EMGS present in all three datasets had significant association with prognosis profile (p<0.05), however, only 4 of these (25%) had a hazard ratio of greater than 1 (Table 7).

TABLE 6

SpMGS genes with significant sensitivity in predicting prognosis in three datasets

| Symbol | HR (gene) | p-value(gene) |
|---|---|---|
| ABCF1 | 2.60 | <0.001 |
| PREB | 2.05 | 0.007 |
| PAPOLA | 2.04 | 0.013 |
| PTDSS1 | 2.00 | <0.001 |
| DOCK7 | 1.87 | <0.001 |
| HSPA9 | 1.79 | 0.023 |
| CORO1C | 1.71 | 0.002 |
| DPP3 | 1.63 | 0.005 |
| ANAPC5 | 1.29 | 0.009 |
| FBXW11 | 1.26 | 0.042 |
| UBE3A | 1.24 | 0.046 |
| ATP6V1C1 | 1.23 | 0.031 |
| D10Wsu52e (HSPC117) | 0.80 | 0.018 |
| XBP1 | 0.68 | <0.001 |
| FOS | 0.66 | 0.013 |
| TOB2 | 0.47 | 0.050 |
| HCRT | 0.43 | 0.046 |

Bold type indicates genes with a hazard ratio greater than 1.

TABLE 7

EMGS genes with significant sensitivity in predicting prognosis in three datasets

| Symbol | HR (gene) | p-value(gene) |
|---|---|---|
| GNAI1 | 2.30 | <0.001 |
| HEPH | 1.85 | 0.012 |
| C9orf58 | 1.43 | 0.031 |
| TGFB1I1 | 1.35 | 0.009 |
| DPEP1 | 0.83 | 0.032 |
| FOLR2 | 0.82 | 0.030 |
| DSP | 0.82 | 0.049 |
| TMEM30B | 0.81 | 0.048 |
| LUM | 0.78 | 0.042 |
| KLF15 | 0.77 | 0.018 |
| TSC22D3 | 0.75 | 0.004 |
| ATP1B1 | 0.73 | 0.003 |
| ELN | 0.69 | 0.006 |
| BHLHB5 | 0.67 | 0.015 |
| CXCL12 | 0.64 | <0.001 |
| SPARCL1 | 0.57 | <0.001 |

Bold type indicates genes with a hazard ratio greater than 1.

The genes with high hazard ratios were considered high yield components of the predictive model. As such, six genes of the twelve gene SpMGS subgroup were selected, and tested for predictive power as a stand alone expression signature. This "6-gene-model" consists of the following genes: Abcf1, Coro1c, Dpp3, Preb, Ptdss1 and Ube3a (Table 8).

TABLE 8

Genes included in the 6-gene model

| Gene Symbol | Gene Name and Description |
|---|---|
| ABCF1 | ATP-binding cassette, sub-family F, member1 This protein may be regulated by tumor necrosis factor-alpha and play a role in enhancement of protein synthesis and the inflammation process |
| CORO1C | Coronin, actin binding protein, 1C This gene encodes a member of the WD repeat protein family. Members of this family are involved in a variety of cellular processes, including cell cycle progression, signal transduction, apoptosis, and gene regulation |
| DPP3 | Dipeptidyl-peptidase 3 This gene encodes a protein that is a member of the S9B family in clan SC of the serine proteases. Increased activity of this protein is associated with certain type of cancers |
| PREB | Prolactin regulatory binding-element protein This protein may act as a transcriptional regulator and is thought to be involved in some of the developmental abnormalities |
| UBE3A | Ubiquitin protein ligase E3A This gene encodes an E3 ubiquitin-protein ligase, part of the ubiquitin protein degradation system |
| PTDSS1 | Phosphatidylserine synthase 1 This gene is related to the phosphorous metabolism and lipid biosynthesis |

Survival analysis on the original three public datasets indicated that the 6-gene model was powerful in predicting patient outcome (FIG. 5A). The six-gene model also predicted survival independent of known clinical variables based on multivariable proportional hazards analysis using the van de Vijver data set (Table 9). The same analysis was performed on three additional independent public datasets to independently validate the model (FIG. 5B). These analyses revealed a significant association between the 6-gene model and relapse-free survival in the GSE1456 and GSE2990 datasets, and overall survival in the GSE7390 dataset by log-rank test (Table 10). In all datasets tested, patients with poor prognosis correlated largely with up-regulation of the 6 genes based on cluster analysis.

TABLE 9

Multivariable Proportional-Hazards Analysis of risk of distant metastasis as first event in van de Vijver's dataset based on 6-gene model

| | HR | p-value |
|---|---|---|
| Six-gene model | 0.30 | <0.00001 |
| Primary tumor size (≤2 cm vs. >2 cm) | 0.56 | 0.006 |

TABLE 9-continued

Multivariable Proportional-Hazards Analysis of risk of distant metastasis as first event in van de Vijver's dataset based on 6-gene model

|  | HR | p-value |
|---|---|---|
| Node (negative vs. positive) | 0.93 | 0.8 |
| Age (<45 vs. ≥45 years) | 1.62 | 0.02 |
| Chemotherapy exposure (no vs. yes) | 1.89 | 0.04 |
| ER (negative vs. positive) | 0.74 | 0.25 |
| Differentiation: | | |
| Intermediate vs. well | 1.15 | 0.61 |
| Poorly vs. well | 1.06 | 0.83 |

TABLE 10

Survival analysis in public datasets based on 6-gene model

| Dataset | p-value (p-SpMGS*) | Clinical End-point |
|---|---|---|
| Original Datasets: | | |
| van de Vijver | 1.03e−009 (1.39e−004) | Overall survival (10 year) |
| GSE4922 | 0.009 (0.05) | Disease-free survival (10 year) |
| GSE2034 | 0.0036 (0.0013) | Relapse-free survival (5 year) |
| Independent Datasets: | | |
| GSE1456 | 0.0009 | Relapse-free survival (5 year) |
| GSE2990 | 0.03 | Relapse-free survival (10 year) |
| GSE7390 | 0.015 | Overall survival (12 year) |

*p-value of survival analysis based on SpMGS

Example 4

Validation of Six-Gene Prognostic Signature in Lung Cancer

This example describes validation of the six-gene prognostic signature in a lung cancer dataset.

Survival analysis was performed on six public datasets utilizing the 6-gene model as described in Example 3.

Lung Cancer Data Sets

GSE4573 Data set:

This was a derivation and validation analysis of a gene signature for the prediction of lung cancer patient outcomes. It consisted of 130 patients with squamous cell carcinomas from all stages (Raponi et al., *Cancer Res.* 66:7466-7472, 2006).

GSE11117 Data Set:

This was a derivation and validation analysis of a gene signature for the prediction of lung cancer patient outcomes. It involved 41 chemotherapy-naive non-small cell lung carcinoma (NSCLC) patients (Baty et al., *Am. J. Respir. Crit. Care Med.* 181:181-188, 2010).

Data sets published by National Cancer Institute director's challenge consortium for the molecular classification of lung adenocarcinoma and Shedden et al. (*Nature Med.* 14:822-827, 2008).

Moffitt Cancer Center Data Set (HLM):

This was a derivation and validation analysis of a gene signature for the prediction of lung cancer patient outcomes. It involved 79 patients with NSCLC of all stages.

University of Michigan Cancer Center Data Set (MICH):

This was a derivation and validation analysis of a gene signature for the prediction of lung cancer patient outcomes. It involved 177 patients with NSCLC of all stages.

The Dana-Farber Cancer Institute Data Set (DFCI):

This was a derivation and validation analysis of a gene signature for the prediction of lung cancer patient outcomes. It involved 82 patients with NSCLC of all stages.

Memorial Sloan-Kettering Cancer Center (MSKCC):

This was a derivation and validation analysis of a gene signature for the prediction of lung cancer patient outcomes. It involved 104 patients with NSCLC of all stages.

As summarized in Table 11, the six-gene model was able to stratify poor from good prognosis with statistical significance in GSE4573 and Moffitt Cancer Center data sets (P=0.04 and P=0.03, respectively). Although the predictions of other data sets (GSE11117, University of Michigan Cancer Center, The Dana-Farber Cancer Institute, and Memorial Sloan-Kettering Cancer Center) were not statistically significant, they trended toward poor prognosis (P=0.09, P=0.08, P=0.07, and P=0.09, respectively) and were well separated by Kaplan-Meier curves (FIG. 6). This indicates that the 6-gene signature can predict outcome in cancer types other than breast cancer.

TABLE 11

Survival analysis in public lung cancer datasets based on 6-gene model

| Dataset | Total # Patients | Kaplan-Meier (p) | HR | Cancer type |
|---|---|---|---|---|
| GSE4573 | 130 | 0.04 | 0.52 | SCC |
| GSE11117 | 41 | 0.09 | 0.51 | NSCLC |
| HLM | 79 | 0.03 | 0.52 | NSCLC |
| MICH | 177 | 0.08 | 0.66 | NSCLC |
| DFCI | 82 | 0.07 | 0.49 | NSCLC |
| MSKCC | 104 | 0.09 | 0.51 | NSCLC |

SCC, squamous cell lung carcinoma; NSCLC, non-small cell lung cancer

Example 5

Prognosis of Cancer

This example describes particular methods that can be used to prognose a subject diagnosed with cancer. However, one skilled in the art will appreciate that methods that deviate from these specific methods can also be used to successfully provide the prognosis of a subject with cancer.

A tumor sample and adjacent non-tumor sample is obtained from the subject. Approximately 1-100 µg of tissue is obtained for each sample type, for example using a fine needle aspirate. RNA and/or protein is isolated from the tumor and non-tumor tissues using routine methods (for example using a commercial kit).

In one example, the prognosis of a tumor (for example, a breast tumor or lung tumor) is determined by detecting expression levels of ABCF1, CORO1C, DPP3, PREB, UBE3A, and PTDSS1 in a tumor sample obtained from a subject by microarray analysis or real-time quantitative PCR. For example, the disclosed gene signature can be utilized. The relative expression level of ABCF1, CORO1C, DPP3, PREB, UBE3A, and PTDSS1 in the tumor sample is compared to the control (e.g., RNA isolated from adjacent non-tumor tissue from the subject). In other cases, the control is a reference value, such as the relative amount of such molecules present in non-tumor samples obtained from a group of healthy subjects or cancer subjects. An increase in expression of five of, or all of ABCF1, CORO1C, DPP3, PREB, UBE3A, and PTDSS1 in the tumor sample relative to the control (such as an increase of at least about 1.5-fold, for example at least about 2-fold, about 2.5-fold, about 3-fold, about 4-fold, about 5-fold, about 7-fold or about 10-fold) indicates a poor prognosis, such as a decrease in the likelihood of survival, for the subject.

In another example, the relative expression of cancer survival factor-associated molecules is determined at the protein level by methods known to those of ordinary skill in the art, such as protein microarray, Western blot, or immunoassay techniques. Total protein is isolated from the tumor sample and control (non-tumor) sample and compared using any suitable technique. An increase in protein expression of five of, or all of ABCF1, CORO1C, DPP3, PREB, UBE3A, and PTDSS1 in the tumor sample relative to the control (such as an increase of at least about 1.5-fold, for example at least about 2-fold, about 2.5-fold, about 3-fold, about 4-fold, about 5-fold, about 7-fold or about 10-fold) indicates a poor prognosis, such as a decrease in the likelihood of survival, for the subject.

Example 6

Diagnosis of Cancer

This example describes particular methods that can be used to diagnose a subject with cancer. However, one skilled in the art will appreciate that methods that deviate from these specific methods can also be used to successfully provide the diagnosis of a subject with cancer.

A tumor sample and adjacent non-tumor sample is obtained from the subject. Approximately 1-100 µg of tissue is obtained for each sample type, for example using a fine needle aspirate. RNA and/or protein is isolated from the tumor and non-tumor tissues using routine methods (for example using a commercial kit).

In one example, the diagnosis of a malignant tumor is determined by detecting expression levels of ABCF1, CORO1C, DPP3, PREB, UBE3A, and PTDSS1 in the tumor sample obtained from a subject by microarray analysis or real-time quantitative PCR. For example, the disclosed gene signature can be utilized. The relative expression level of ABCF1, CORO1C, DPP3, PREB, UBE3A, and PTDSS1 in the tumor sample is compared to the control (e.g., RNA isolated from adjacent non-tumor tissue from the subject). In other cases, the control is a reference value, such as the relative amount of such molecules present in non-tumor samples obtained from a group of healthy subjects or cancer subjects. An increase in expression of five of, or all of ABCF1, CORO1C, DPP3, PREB, UBE3A, and PTDSS1 in the tumor sample relative to the control (such as an increase of at least about 1.5-fold, for example at least about 2-fold, about 2.5-fold, about 3-fold, about 4-fold, about 5-fold, about 7-fold or about 10-fold) indicates the presence of a malignant tumor in the subject.

In another example, the relative expression of cancer survival factor-associated molecules is determined at the protein level by methods known to those of ordinary skill in the art, such as protein microarray, Western blot, or immunoassay techniques. Total protein is isolated from the tumor sample and control (non-tumor) sample and compared using any suitable technique. An increase in protein expression of five of, or all of ABCF1, CORO1C, DPP3, PREB, UBE3A, and PTDSS1 in the tumor sample relative to the control (such as an increase of at least about 1.5-fold, for example at least about 2-fold, about 2.5-fold, about 3-fold, about 4-fold, about 5-fold, about 7-fold or about 10-fold) indicates the presence of a malignant tumor in the subject.

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

We claim:

1. A method of detecting gene expression in a subject with a tumor, comprising:
   contacting a tumor sample obtained from the subject with the tumor with probes for each cancer survival factor-associated molecules consisting of all of the cancer survival factor-associated molecules listed in Table 1 and performing real time quantitative polymerase chain reaction analysis; or
   contacting a tumor sample obtained from the subject with the tumor with a microarray comprising probes for each cancer survival factor-associated molecules consisting of all of the cancer survival factor-associated molecules listed in Table 1 and performing microarray analysis.

2. The method of claim 1, wherein the tumor sample obtained from the subject with the tumor is from a breast tumor, a lung tumor, a prostate tumor, or a colorectal tumor.

3. The method of claim 1, further comprising detecting expression of 1 to 10 housekeeping genes.

4. The method of claim 1, further comprising comparing expression of the cancer survival factor-associated molecules in the tumor sample to a non-tumor control.

5. A method comprising:
   measuring expression of at least five cancer survival factor-associated molecules selected from the group consisting of ABCF1, CORO1C, PREB, DPP3, UBE3A, and PTDSS1 in a tumor sample obtained from the subject with the tumor;
   determining prognosis of the subject with the tumor by comparing expression of the at least five cancer survival factor-associated molecules in the tumor sample to a non-tumor control, wherein an at least 1.5-fold up-regulation in expression of the at least five cancer survival factor-associated molecules relative to the non-tumor control indicates that the subject has a poor prognosis, and wherein no significant change in the expression of the at least five cancer survival factor-associated molecules relative to the non-tumor control indicates that the subject has a good prognosis; and
   administering to the subject an effective amount of an agent that alters expression or activity of one or more of the at least five cancer survival factor-associated molecules selected from the group consisting of ABCF1, CORO1C, PREB, DPP3, UBE3A, and PTDSS1 having an at least 1.5-fold up-regulation in expression relative to the non-tumor control, wherein the agent is an antisense or antibody.

6. The method of claim 5, wherein the at least five cancer survival factor-associated molecules comprise all of the cancer survival factor-associated molecules in Table 1.

7. The method of claim 5, wherein expression of the at least five cancer survival factor-associated molecules is measured by real time quantitative polymerase chain reaction or microarray analysis.

8. The method of claim 5, wherein the tumor is a breast tumor, a lung tumor, a prostate tumor, or a colorectal tumor.

9. The method of claim 5, further comprising detecting expression of 1 to 10 housekeeping genes.

10. The method of claim 5, wherein the poor prognosis comprises decreased overall survival, decreased relapse-free survival, or decreased metastasis-free survival.

11. The method of claim 5, wherein the good prognosis of the subject comprises increased chance of survival.

12. The method of claim 5, wherein the poor prognosis of the subject comprises diagnosis with a malignant tumor.

13. The method of claim 5, wherein the good prognosis of the subject comprises diagnosis with a benign tumor.

14. The method of claim 5, further comprising administering to the subject one or more of surgery, radiation therapy, or chemotherapy.

\* \* \* \* \*